United States Patent [19]
Gobbini et al.

[11] Patent Number: 5,521,167
[45] Date of Patent: May 28, 1996

[54] CYCLOPENTANPERHYDRO-PHENANTHREN-17β-(HYDROXY OR ALKOXY)-17α-(ARYL OR HETEROCYCLYL)-3β-DERIVATIVES ACTIVE ON THE CARDIOVASCULAR SYSTEM, AND PHARMACEUTICAL COMPOSITIONS CONTAINING SAME

[75] Inventors: Mauro Gobbini, Mercallo; Mara Ferrandi; Marco Frigerio, both of Milan; Piero Melloni, Bresso; Marco Torri, Rho; Loredana Valentino, Buccinasco, all of Italy

[73] Assignee: Sigma-Tau Industrie Farmceutiche Riunite S.p.A., Rome, Italy

[21] Appl. No.: 128,128

[22] Filed: Sep. 29, 1993

[30] Foreign Application Priority Data

Sep. 29, 1992 [DE] Germany ............ 42 32 656.7

[51] Int. Cl.⁶ ................. C07J 1/00; A61K 31/565
[52] U.S. Cl. ................. 514/172; 540/94; 540/95; 540/109; 514/176
[58] Field of Search ............... 514/176, 172; 540/95, 109, 94

[56] References Cited

U.S. PATENT DOCUMENTS

| | | | |
|---|---|---|---|
| 4,203,981 | 5/1980 | Pierdet et al. | 540/95 |
| 4,447,425 | 5/1984 | Carlyle et al. | 540/95 |
| 5,252,630 | 10/1993 | Gerhart et al. | 540/95 |
| 5,380,839 | 1/1995 | McCall et al. | 540/111 |
| 5,432,169 | 7/1995 | Guadri et al. | 514/172 |
| 5,444,055 | 8/1995 | Cessi et al. | 514/182 |

OTHER PUBLICATIONS

Minato et al, J. Chem. Soc 377 (1966).
Jorghensen, Biochemica & Biophysica Acta 356 36(1974).
Doucet et al, Am. J. Physiol. 251 851 (1986).
Elisberg et al, JACS vol. 74 2814 (1952).
D'Incan et al. Tetrahedron vol. 38 1755 (1982).
Swann et al, Tetahedron 20 265 (1964).
Swann et al, Tetrahedron 22 231 (1966).

*Primary Examiner*—Nicholas Rizzo
*Attorney, Agent, or Firm*—Oblon, Spivak, McClelland, Maier & Neustadt

[57] ABSTRACT

The present invention relates to new cyclopentanperhydrophenanthren-17-(hydroxy or alkoxy)-17-(aryl or heterocyclyl)-3β-derivatives, active on the cardiovascular system, to a process for their preparation and to pharmaceutical compositions containing them. The invention relates to compounds of general formula (I)

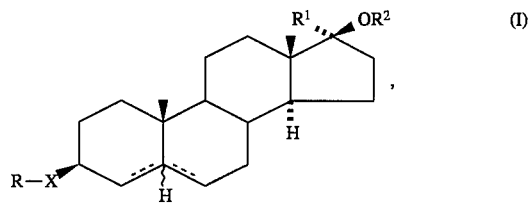

wherein X is O or S and R, $R^1$ and $R^2$ is selected from various groups.

9 Claims, No Drawings

CYCLOPENTANPERHYDROPHENANTHREN-17β-(HYDROXY OR ALKOXY)-17α-(ARYL OR HETEROCYCLYL)-3β-DERIVATIVES ACTIVE ON THE CARDIOVASCULAR SYSTEM, AND PHARMACEUTICAL COMPOSITIONS CONTAINING SAME

The invention relates to new cyclopentanperhydrophenanthren-17-(hydroxy or alkoxy)- 17-(aryl or heterocyclyl)-3β-derivatives, active on the cardiovascular system, to a process for their preparation and to pharmaceutical compositions containing them.

The invention relates to compounds of general formula (I)

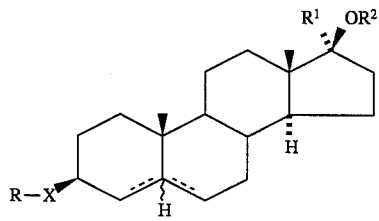

wherein:

the symbol ∼∼∼ means that the hydrogen in position 5 can have an α or β configuration.

the symbol --- represents either a single or a double bond;

X is O or S;

R is C2–C6 alkyl or C3–C6 alkenyl, substituted by a quaternary ammonium group or one or more $OR^3$, $NR^4R^5$ or $C(NH)NR^6R^7$, wherein $R^3$ is C2–C4 alkyl substituted by an aldehyde group, one or more $NR^6R^7$ or by $NR^6R^7$ and hydroxy;

$R^4$, $R^5$ are independently hydrogen, methyl, C2–C6 alkyl or C3–C6 alkenyl unsubstituted or substituted by one or more $NR^6R^7$, or $NR^6R^7$ and hydroxy, or $R^4$ and $R^5$ taken together with the nitrogen atom form an unsubstituted or substituted saturated or unsaturated five- or six-membered heteromonocyclic ring optionally containing another heteroatom chosen from oxygen or sulfur or nitrogen, or $R^4$ is hydrogen and $R^5$ is $C(NH)NH_2$;

$R^6$, $R^7$ are independently hydrogen, C1–C4 alkyl optionally substituted by one or more hydroxy or amino group, or $R^6$ and $R^7$ taken together form, with the nitrogen they are linked to, a saturated or unsaturated five o six - membered monoheterocyclic ring;

$R^1$ is an aryl group or a saturated or unsaturated monoheterocyclic ring, containing one or more heteroatom selected from oxygen, sulfur and nitrogen, unsubstituted or substituted by one or more halogen, hydroxy, alkoxy, amino, alkylamino, dialkylamino, C1–C6 lower alkyl group with the proviso that $R^1$ is not 4-hydroxy-2-butenoic acid lactone;

$R^2$ is hydrogen, methyl, C2–C6 alkyl or C3–C6 alkenyl, unsubstituted or substituted by a quaternary ammonium group or one or more $OR^{3,}$ $NR^4R^5$, $C(NH)NR^6R^7$.

Also the pharmaceutically acceptable salts as well as the optical antipodes, i.e. the enantiomers, the racemic mixture of the optical antipodes, or other mixtures thereof, the geometric isomers and their mixtures, the diastereoisomers and mixtures of diastereoisomers of compounds of general formula (I) are included in the scope of the invention.

Also comprised in the scope of the invention are the metabolites and the metabolic precursors of compounds of general formula (I).

Pharmaceutically acceptable salts of (I) are salts which retain the biologically activity of the base or the acid and are derived from such known pharmacologically acceptable acids such as hydrochloric, sulphuric, phosphoric, malic, tartaric, maleic, citric, methanesulphonic or benzoic acids.

The aryl group is preferably phenyl and the substituents preferably methyl, ethyl, isopropyl, methoxy, dimethoxy, methylendioxy, bromo, chloro, dimethylamino.

The saturated or unsaturated mono-heterocyclic ring is preferably 1,3-dithian-2-yl, furyl, tetrahydrofuryl, thienyl, pyrrolyl, pyridyl, pyridyl-N-oxide, pyrimidyl, pyridazynil, piperidyl, 2-oxo-(1H)-pyridyl, 2-oxo-(2H)-5-pyranyl, 2-oxo-(5H)-4-pyrrolyl, 1-amino-2-oxo-(5H)-3-pyrrolyl, or an imidazolyl, thiazolyl, oxazolyl ring.

The alkyl and alkenyl groups may be branched or straight chain groups.

The C1–C6 alkyl group is preferably a C1–C4 alkyl group, e.g. methyl, ethyl, propyl, isopropyl, butyl, sec-butyl.

The C2–C6 alkyl group is preferably a C2–C4 alkyl group, e.g. ethyl, propyl, isopropyl, butyl, sec-butyl.

The C3–C6 alkenyl group is preferably a C3–C4 alkenyl group.

The quaternary ammonium group is preferably a trimethylammonium- or a N-methylpyrrolidinium- or a methylpiperidinium- group.

The $OR^3$ group is preferably 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The $NR^4$ $R^5$ group is preferably amino, methylamino, ethylamino, propylamino, isopropylamino, allylamino, propargylamino, dimethylamino, pyrrolidinyl, morpholinyl, piperazinyl, 1-imidazolyl, 1-guanidyl 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)2-hydroxypropylamino, 2,3-diaminopropylamino, ( 2-1-pyrrolidinyl)ethyl)methylamino.

The $NR^6R^7$ group is preferably amino, methylamino, ethylamino, propylamino, isopropylamino, allylamino, propargylamino, dimethylamino, pyrrolidinyl, morpholino, piperazinyl, 1-imidazolyl, 1-guanidyl, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl) 2-hydroxypropylamino, 2,3-diaminopropylamino, (2-(1-pyrrolidinyl)ethyl)methylamino.

The $C(NH)NR^6R^7$ group is preferably a primary amidino group.

Preferred examples of specific compounds according to the present invention are

3β-(2-Aminoethoxy)-17α-(3-furyl)-5β-androstan-17β-ol

3β-(3-Aminopropoxy)-17α-(3-furyl)-5β-androstan-17β-ol

3β,17β-Bis(2-aminoethoxy)-17α-(3-furyl)-5β-androstane

3β-(2-Aminoethoxy)-17β-(2-(1-pyrrolidinyl)ethoxy)-17α-(3-furyl)-5β-androstane

3β-(2-(1-Pyrrolidinyl)ethoxy)-17α-(3-furyl)-5β-androstan-17β-ol

3β-(2-(1-Pyrrolidinyl)ethoxy)-17β-(2-aminoethoxy)-17α-(3-furyl)-5β-androstane

3β,17β-Bis(2-(1-pyrrolidinyl)ethoxy)-17α-(3-furyl)-5β-androstane

3β-(2-(2-(1-Pyrrolidinyl)ethoxy)ethoxy)-17α-(3-furyl)-5β-androstan-17β-ol

3β-(2-(2-(1-Pyrrolidinyl)ethoxy)ethoxy)-17β-(2-aminoethoxy)- 17α-(3-furyl)-5β-androstane 3β-(2-(2-(1-Pyrrolidinyl)ethoxy)ethoxy)-17β-(2-( 1-pyrrolidinyl)ethoxy)-17α-(3-furyl)-5β-androstane 3β-(2-Aminoethoxy)-17α-(3-furyl)-androstan-17β-ol 3β-(3-Aminopropoxy)-17α-(3-furyl)-androstan-17β-ol 3β,17β-Bis(2-aminoethoxy)-17α-(3-furyl)-androstane 3β-(2-Aminoethoxy)-17β-(2-(1-pyrrolidinylethoxy)-17α-(3-furyl)-androstane 3β-(2-(1-Pyrrolidinyl)ethoxy)-17α-(3-furyl)-androstan-17β-ol 3β-(2-(1-Pyrrolidinyl)ethoxy)-17β-(2-aminoethoxy)-17α-(3-furyl)-androstane 3β,17β-Bis(2-(1-pyrrolidinyl)ethoxy)-17α-(3-furyl)-androstane 3β-(2-(2-(1-Pyrrolidinyl)ethoxy)ethoxy)-17α-(3-furyl)-androstan-17β-ol 3β-(2-(2-(1-Pyrrolidinyl)ethoxy)ethoxy)-17β-(2-aminoethoxy)- 17α-(3-furyl)-androstane 3β-(2-(2-(1-Pyrrolidinyl)ethoxy)ethoxy)-17β-(2-( 1-pyrrolidinyl)ethoxy)-17α-(3-furyl)-androstane 3β-(2-Aminoethoxy)-17α-(3-furyl)-androst-4-en-17β-ol 3β,17β-Bis(2-aminoethoxy)-17α-(3-furyl)-androst-4-ene 3β-(2-Aminoethoxy)-17β-(2-(1-pyrrolidinylethoxy)-17α-(3-furyl)-androst-4-ene 3β-(2-(1-Pyrrolidinyl)ethoxy)-17α-(3-furyl)-androst-4-en-17β-ol 3β-(2-(1-Pyrrolidinyl)ethoxy)-17β-(2-aminoethoxy)-17α-(3-furyl)-androst-4-ene 3β,17β-Bis(2-(1-pyrrolidinyl)ethoxy)-17α-(3-furyl)-androst-4-ene 3β-(2-(2-(1-Pyrrolidinyl)ethoxy)ethoxy)-17α-(3-furyl)-androst-4-en-17β-ol 3β-(2-(2-(1-Pyrrolidinyl)ethoxy)ethoxy)-17β-(2-aminoethoxy)- 17α-(3-furyl)-androst-4-ene 3β-(2-(2-(1-Pyrrolidinyl)ethoxy)ethoxy)-17β-(2-(1-pyrrolidinyl)ethoxy- 17α-(3-furyl)-androst-4-ene 3β-(2-Aminoethoxy)-17α-(3-furyl)-androst-5-en-17β-ol 3β-(3-Aminoepropoxy)-17α-(3-furyl)-androst-5-en-17β-ol 3β,17β-Bis(2-aminoethoxy)-17α-(3-furyl)-androst-5-ene 3β-(2-Aminoethoxy)-17β-(2-(1-pyrrolidinylethoxy)-17α-(3-furyl)-androst-5-ene 3β-(2-(1-Pyrrolidinyl)ethoxy)-17α-(3-furyl)-androst-5-en-17β-ol 3β-(2-(1-Pyrrolidinyl)ethoxy)-17β-(2-aminoethoxy)-17α-(3-furyl)-androst-5-ene 3β-,17β-Bis(2-(1-pyrrolidinyl)ethoxy)-17α-(3-furyl)-androst-5-ene 3β-(2-(2-(1-Pyrrolidinyl)ethoxy)ethoxy)-17α-(3-furyl)-androst-5-en-17β-ol 3β-(2-(2-(1-Pyrrolidinyl)ethoxy)ethoxy)-17β-(2-aminoethoxy)-17α-( 3-furyl)-androst-5-ene 3β-(2-(2-(1-Pyrrolidinyl)ethoxy)ethoxy)-17β-(2-(1-pyrrolidinyl)ethoxy)-17α-( 3-furyl)-androst-5-ene Preferred compounds are also the corresponding 17α-(3-thienyl)-, 17α-(4-chlorophenyl)-, 17α-(4-methoxyphenyl)-, 17α-(3,4-dimethoxyphenyl)-, 17α-(3,4-methylendioxyphenyl)-derivatives and the derivatives wherein X=S.

The invention furthermore provides a process for the preparation of said compounds (I) which comprises the condensation of compounds having, general formula (II)

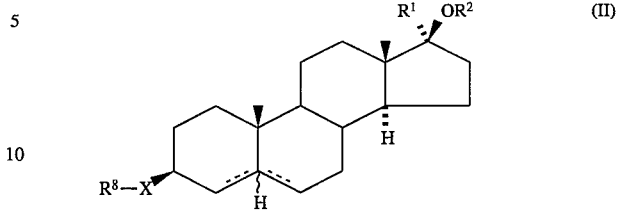

wherein $R^1$ and $R^2$ are as above defined, and $R^8$ is hydrogen or a protective group for the hydroxy or mercapto functions, and in this case $R^2$ is different from H, with a compound of general formula (III)

R—Y          (III)

wherein Y is an electron-withdrawing group, such as halogen, mesyloxy, or tosyloxy group, and R is as above defined, the free hydroxy and amino groups, if any, present in R being protected with known methods to give, if necessary after removal of protective groups, if any, present in R, a compound of general formula (I) which may be converted into another compound of general formula (I) and optionally converting compounds (I)into a pharmaceutically acceptable salt and, in case, separating a mixture of isomers into single isomers.

When in the starting compounds of general formula (II) $R^2$=H, compounds of general formula (I) where $R^2$ is either hydrogen or $R^2$=R are obtained: when in the starting compounds of general formula (II) $R^2$ is different from H, compounds of general formula (I) where $R^2$ can be different from R are obtained Compounds of general formula (II)where $R^2$=H are known compounds such as, for example: 17α-(3-furyl)-5β-androstane-3β,17β-diol and 17α-(3-furyl)-androstane-3β,17β-diol (U.S. Pat. No. 3,436,390) or are obtained by reacting aryl or heterocyclyl metallorganics with compounds (IV),

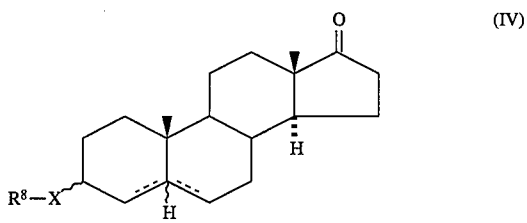

where $R^8$ is as above defined.

The reactions of the aryl or heterocyclyl organometallics, i.e. lithium, or magnesium or cerium halides, or zirconium or titanium alkoxydes, with compounds of general formula (IV) are best carried out in an inert aprotic solvent, such as tetrahydrofuran, ethyl ether or dioxane at a temperature ranging from −78° C. to room temperature.

Compounds (IV) are known compounds such as e.g. 3β-hydroxy-5β-androstan-17-one, 3β-hydroxyandrostan-17-one (Elisberg E. et al., *J. Amer. Chem. Soc.*, 1952, 74, 2814); 3β-hydroxyandrost-4-en-17-one, 3α-hydroxyandrost-4-en-17-one (D'Incan E. et al., *Tetrahedron*, 1982, 38, 1755); 3β-hydroxyandrost-5-en-17-one (Coffey S. in Rodd's Chemistry of Carbon Compounds, 1970, IID, 257); 3β-mercapto-5β-androstan-17-one, 3β-mercaptoandrostan-17-one, 3β-mercaptoandrost-5-en-17-one (Swann D. A. and Turnbull J. H., *Tetrahedron*, 1964, 20, 265 and *Tetrahedron*, 1966, 22, 231) or are obtained from the known compounds (IV) by known methods.

For example an unknown 3β-mercapto derivative can be obtained e.g. by ammonolysis of the corresponding acetylthio derivative (V)

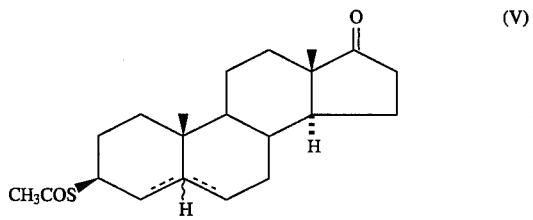

which in turn is obtained by reaction of the corresponding 3α-hydroxy derivative with thiolacetic acid in the presence of a dialkyl azodicarboxylate and triphenylphosphine.

Compounds of general formula (II) where $R^2$ is different from H and R8=H are obtained from compounds of general formula (II) where $R^2$=H and $R^8$=protective group, by condensation with a compound of general formula (VI) where $R^2$ is different from H and Y is above defined and removing the protective group with known methods.

$$R^2-Y \quad (VI)$$

The condensation reactions between (II), where $R^2$ is as above defined, and (III) or between (II), where $R^2$ is hydrogen, and (VI) are best carried out in an inert aprotic solvent, such as tetrahydrofuran, dioxane, dimethylformamide, dimethylsulfoxyde or in the neat (III)or (VI) and in the presence of a strong base e.g. sodium or potassium hydride at a temperature ranging from 10° C. to about 110° C.

The purification is best performed by flash-chromatography on silica gel.

The compounds of general formula (III) or (VI) are known compounds, often commercially available or preparable from known compounds by known methods.

The derivatives (I), prepared according to the invention and their pharmaceutically acceptable salts have much reduced toxicity compared to the known 17β-(3-furyl)-5β-androstane- 3β, 14β-diol (Ref. comp.) (Minato H. and Nagasaki T., *J. Chem. Soc.* (C), 1966, 377) and are useful agents for the treatment of cardiovascular disorders such as heart failure and hypertension. Moreover said compounds (I) show higher affinity for the receptor site of the $Na^+,K^+$-ATPase than (Ref. comp.)and behave as partial agonists on the enzymatic activity of the $Na^+,K^+$-ATPase.

To test the affinity for the receptor site of the $Na^+,K^+$-ATPase and the agonist or antagonist activity on the enzyme, the following tests were used: a) displacement of the specific $^3$H-ouabain binding from the $Na^+,K^+$-ATPase receptor purified according to Jorghensen (Jorghensen P., BBA, 1974, 356, 36) and Erdmann ( Erdmann E. et al., *Arzneim. Forsh.*, 1984, 34, 1314); b) inhibition of the activity of the purified $Na^{+,K+}$-ATPase measured as % of hydrolysis of $^{32}$P-ATP in presence and in absence of the tested compound (Doucet A. et al., *Am. J. Physiol.*, 1986, 251, F851). The ability of these compounds to lower blood pressure in adult hypertensive MHS rats was tested according to the following scheme: systolic blood pressure (SBP) and heart rate (HR) were measured by an indirect tail-cuff method in three-month old hypertensive MHS rats before starting with the treatment (basal values). The rats were then subdivided in two groups of 7 animals each, one receiving the compound and the other, the control group, receiving only the vehicle. The compound was orally daily given, suspended in Methocel 0.5% (w/v), for ten days. SBP and HR were measured daily 6 and 24 hours after the treatment.

After ten-day treatment, washout was started for at least two days, to verify whether the treatment maintained SBP low or reestablished the basal values.

The affinity and the inhibitory activity of some basic ethers, thioethers and of the Ref. comp. in the two tests are shown in the following table:

| Compound | Binding $^3$H-Ouab. Displacement -log IC$_{50}$ | Inhibitory Activity -log IC$_{50}$ |
|---|---|---|
| Ref. comp. | 6.3 | 5.7 |
| Comp. I-aa | 6.7 | 5.7 |
| Comp. I-ad | 6.4 | 5.5 |
| Comp. I-ai | 6.6 | 5.8 |
| Comp. I-ak | 6.4 | 5.3 |
| Comp. I-al | 6.3 | 5.8 |
| Comp. I-am | 6.7 | 5.8 |
| Comp. I-an | 6.5 | 5.5 |
| Comp. I-aq | 6.5 | 5.6 |
| Comp. I-ay | 6.4 | 5.8 |
| Comp. I-ca | 6.5 | 5.7 |

The activity of the Ref. comp. and some basic ethers and thioethers in preventing the development of hypertension is shown in the following table:

| SYSTOLIC BLOOD PRESSURE FALL IN SPONTANEOUS HYPERTENSIVE RATS (MHS) | | | |
|---|---|---|---|
| Compound | RATS | DOSE* mg/Kg/ os | SBP mm Hg | HR beats/min. |
| Controls | 7 | Methocel | 171 +/- 4.5 | 384 +/- 11.0 |
| Ref. comp. | 7 | 20 | 173 +/- 4.0 | 380 +/- 10.0 |
| Comp. I-am | 7 | 20 | 153 +/- 5.1 | 378 +/- 8.5 |
| Comp. I-an | 7 | 20 | 152 +/- 5.0 | 375 +/- 9.0 |
| Comp. I-aq | 7 | 20 | 148 +/- 3.2 | 388 +/- 12.0 |
| Comp. I-ay | 7 | 20 | 149 +/- 4.8 | 395 +/- 10.0 |

*in METHOCEL 0.5% w/v

The following examples illustrate the invention without limiting it.

EXAMPLE 1

3β-(2-Aminoethoxy)-17α-(3-furyl)-5β-androstan-17β-ol (I-aa)

A solution of 0.162 ml of diethyl azodicarboxylate was added dropwise, under nitrogen, to a solution of 0.42 g of 3β-(2-hydroxyethoxy)-17α-(3-furyl)- 5β-androstan-17β-ol ((prepared as described in Prep. 1 starting from 3β-(2-hydroxyethoxy)-5β-androstan-17-one which in turn is obtained as described in Prep. 3 starting from 3β-hydroxy-5β-androstan-17-one (Elisberg E. et al., *J. Amer. Chem. Soc.*, 1952, 74, 2814)), 0.146 g of phthalimide and 0.26 g of triphenylphosphine in 2 ml of tetrahydrofuran at room temperature. After 2 hrs the solvent was removed under reduced pressure and the crude product was purified by flash chromatography (SiO$_2$) using n-hexane/ethyl acetate 80/20 to give 0.36 g of 3β-(2-phthalimidoethoxy)-17α-(3-furyl)-5β-androstane-17β-ol as a white solid.

$^1$H-NMR (300 MHz, CDCl$_3$, ppm from TMS): 0.71 (3H, s); 0.94 (3H, s); 3.28–3.40 (2H, m); 3.56 (1H, bs); 3.92 (2H, t); 6.38 (1H, bs); 7.26 (1H, bs); 7.48 (1H, bs); 7.67–7.92 (4H, m).

To a solution of 0.36 g of 3β-(2-phthalimidoethoxy)-17α-(3-furyl)-5β-androstane- 17β-ol in 25 ml of ethanol, 0.16 g of hydrazine hydrate were added at room temperature. The mixture was kept at reflux temperature for 4 hrs, then 5 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.20 g of the title compound (I-aa) as a white pasty solid.

$^1$H-NMR (300 MHz, CDCl$_3$, ppm from TMS): 0.71 (3H, s); 0.96 (3H, s); 2.81–2.92 (2H, t); 3.37–3.48 (2H, t); 3.61 (1H, bs); 6.39 (1H, bs); 7.25 (1H, bs); 7.48 (1H, bs).

EXAMPLE 2

3β-(3-Aminopropoxy)-17α-(3-furyl)-5β-androstan-17β-ol (I-ab)

To a suspension of 0.52 g of NaH (60 % dispersion in mineral oil) in 25 ml of dry tetrahydrofuran 1.60 g of 17α-(3-furyl)-5β-androstane-3β, 17β-diol (U.S. Pat. No. 3,436,390) were added at room temperature, under nitrogen atmosphere and the resulting mixture was refluxed for half an hr; 1.50 g of allyl bromide were added and the reflux continued for half an hr. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography (SiO$_2$) using n-hexane/ethyl acetate 80/20 as eluant to give 0.72 g of 3β-(prop-2-enoxy)- 17α-(3-furyl)-5β-androstane-17β-ol as a dense oil.

$^1$H-NMR (300 MHz, CDCl$_3$, ppm from TMS): 0.70 (3H, s); 0.95 (3H, s); 3.62 (1H, bs); 3.96 (2H, m); 5.10–5.37 (2H, m); 5.82–6.05 (1H, m); 6.38 (1H, bs); 7.25 (1H, bs); 7.48 (1H, bs).

To a solution of 0.24 g of 9-borabicyclo[3.3.1]nonane in 300 ml of dry tetrahydrofuran, 0.68 g of 3β-(prop-2-enoxy)-17α-(3-furyl)-5β-androstane-17β-ol in 20 ml of tetrahydrofuran were added under nitrogen atmosphere, at room temperature. The solution was stirred for 6 hrs, then 1.2 ml of ethanol, 0.4 ml of 6N sodium hydroxide and 0.8 ml of 30% hydrogen peroxide were added. The mixture was stirred at 50° C. for an hr, quenched with a solution of 1.2 g of potassium carbonate in 32 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 0.42 g of 3β-(3-hydroxypropoxy)-17α-( 3-furyl)-5β-androstane-17β-ol as a white solid.

$^1$H-NMR (300 MHz, CDCl$_3$, ppm from TMS): 0.70 (3H, s); 0.95 (3H, s); 3.52–3.68 (3H, m); 3.82 (2H, t); 6.38 (1H, bs); 7.26 (1H, bs); 7.48 (1H, bs).

A solution of 0.16 ml of diethyl azodicarboxylate was added dropwise, under nitrogen, to a solution of 0.40 g of 3β-( 3-hydroxypropoxy)-17α-(3-furyl)-5β-androstane-17β-ol, 0.14 g of phthalimide and 0.24 g of triphenylphosphine in 3 ml of tetrahydrofuran at room temperature. After 2 hrs the solvent was removed under reduced pressure and the crude product was purified by flash-chromatography (SiO$_2$) using n-hexane/ethyl acetate 80/20 to give 0.36 g of 3β-( 3-phthalimidopropoxy)-17α-(3-furyl)-5β-androstane-17β-ol as a pale yellow solid.

$^1$H-NMR (300 MHz, CDCl$_3$, ppm from TMS): 0.71 (3H, s); 0.94 (3H, s); 3.38–3.47 (2H, m); 3.56 (1H, bs); 3.82 (2H, t); 6.38 (1H, bs); 7.26 (1H, bs); 7.48 (1H, bs); 7.71–7.94 (4H, m).

To a solution of 0.36 g of 3β-(3-phthalimidopropoxy)-17α-(3-furyl)-5β-androstane-17β-ol in 25 ml of ethanol, 0.16 g of hydrazinc hydrate were added at room temperature. The mixture was kept at reflux temperature for 4 hrs, then 5 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.18 g of the title compound (I-ab) as a white pasty solid.

$^1$H-NMR (300 MHz, CDCl$_3$, ppm from TMS): 0.71 (3H, s); 0.96 (3H, s); 2.78–2.88 (2H, t); 3.41–3.50 (2H, t); 3.60 (1H, bs); 6.39 (1H, bs); 7.25 (1H, bs); 7.48 (1H, bs).

EXAMPLE 3

3β-(2-(1-Pyrrolidinyl)ethoxy)-17α-(3-furyl)-5β-androstan-17β-ol (I-ac)

To a suspension of 0.80 g of NaH (60% dispersion in mineral oil) in 85 ml of dry tetrahydrofuran 1.0 g of 17α-(3-furyl)- 5β-androstane-3β, 17β-diol (U.S. Pat. No. 3,436,390) were added at room temperature under nitrogen atmosphere. The mixture was kept at 40° C. for 2 hrs, then 3.2 g of 1-(2-chloroethyl)pyrrolidine were added and the suspension was kept at the same temperature for 4 hrs; 50 ml of water were added cautiously and the tetrahydrofuran was distilled at reduced pressure. The residue was extracted with methylene chloride, the organic layer was dried over anhydrous sodium sulfate and evaporated to dryness under reduced pressure. The crude product was purified by flash-chromatography (SiO$_2$) using methylene chloride/methanol 70/30 as eluant to give 0.71 g of the title compound (I-ac), as a white solid.

$^1$H-NMR (300 MHz, CDCl$_3$, ppm from TMS): 0.81 (3H, s); 1.02 (3H, s); 2.46–2.86 (6H, m); 2.64–2.80 (3H, m); 3.53 (1H, bs); 3.75 (2H, t); 6.38 (1H, bs); 7.24 (1H, bs); 7.38 (1H, bs).

EXAMPLE 4

3β17β-Bis(2-(1-pyrrolidinyl)ethoxy)-17α-(3-furyl)-5β-androstane (I-ad)

The title compound (I-ad) (0.25 g) was obtained as a pale yellow solid from 17α-(3-furyl)-5β-androstane-3β, 17β-diol (0.40 g) (U.S. Pat. No. 3,436,390) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.91 (3H, s); 0.95 (3H, s); 2.48–2.65 (12H, m); 3.18–3.42 (3H, m); 3.45–3.64 (2H,m); 6.31 (1H, bs); 7.20 (1H, bs); 7.35 (1H, bs).

EXAMPLE 5

3β-(2-(2-(1-Pyrrolidinyl)ethoxy)ethoxy)-17α-(3-furyl)-5β-androstan-17β-ol (I-ae)

The title compound (I-ae) (0.65 g) was obtained as a pale yellow solid from 3β-(2-hydroxyethoxy)-17α-(3-furyl)-5β-androstan-17β-ol (0.60 g) using the same procedure described in Ex. 3 and using 1-(2-chloroethyl)pyrrolidine as reactant. $^1$H-NMR (300 MHz, CDCl$_3$, ppm from TMS): 0.83 (3H, s); 1.03 (3H, s); 2.46–2.85 (6H, m); 3.38–3.76 (7H, m); 6.39 (1H, bs); 7.25 (1H, bs); 7.37 (1H, bs).

EXAMPLE 6

3β-(2-(2-(1-Pyrrolidinyl)ethoxy)ethoxy)-17β-(2aminoethoxy)- 17α-(3-furyl)-5β-androstane (I-af)

To a suspension of 5.5 g of NaH (60% dispersion in mineral oil) in 400 ml of dry tetrahydrofuran 7.0 g of 3β-(2-tert-butyldimethylsilyloxyethoxy)-17α-(3-furyl)-5α-androstan-17β-ol (prepared as described in Prep. 1 starting from 3β-(2-hydroxyethoxy)-5β-androstan-17-one) were added at room temperature in a nitrogen atmosphere The mixture was kept at 40° C. for 2 hrs, then 26 ml of bromoacetaldehyde diethylacetal were added and the suspension was kept at the same temperature for 4 hrs; 50 ml of water were added cautiously, and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$) using n-hexane/ethyl acetate 80/20 as eluant to give 6.9 g of 3β-(2-tert-butyldimethylsilyloxyethoxy)- 17β-(2,2-diethoxyethoxy)-17α-(3-furyl)-5β-androstane as a thick oil.

$^1$H NMR (300 MHz, CDCl$_3$, ppm from TMS): 0.06 (6H, s); 0.81–0.90 (12H, m); 1.03 (3H, s); 3.46–3.83 (11H, m); 4.68 (1H, t); 6.31 (1H, bs); 7.21 (1H, bs); 7.36 (1H, bs).

A solution of 6.8 g of 3β-(2-tert-butyldimethylsilyloxyethoxy)- 17β-(2,2-diethoxyethoxy)-17α-(3-furyl)-5β-androstane, in 300 ml of dioxane and 230 ml of a saturated solution of tartaric acid was heated at 70° C. for 2 hrs in a nitrogen atmosphere, 100 ml of water were then added and the residue was extracted with methylene chloride. The organic layer was washed with water, dried over anhydrous sodium sulfate and evaporated to dryness under reduced pressure. The crude product was purified by flash-chromatography (SiO$_2$) using as eluant n-hexane/ethyl acetate 70/30 to give 5.0 g of 3β-( 2-tert-butyldimethylsilyloxy-ethoxy)-17β-formylmethoxy-17α-(3-furyl)-5β-androstane as a white solid.

$^1$H NMR (300 MHz, CDCl$_3$, ppm from TMS): 0.06 (6H, s); 0.81–0.90 (12H, m); 1.02 (3H, s); 3.46–3.62 (5H, m); 4.03 (1H, bs); 6.31 (1H, bs); 7.20 (1H, bs); 7.37 (1H, bs); 9.78 (1H, bs).

To a solution of 4.0 g of 3β-(2-tert-butyldimethylsilyloxyethoxy)- 17β-formylmethoxy-17α-(3-furyl)-5β-androstane in 100 ml of methanol, 0.60 g of sodium borohydride were added slowly at 0° C. After ½ hr the temperature of the mixture was left to rise to 25° C. After 2 hrs 20 ml of water were added, the methanol was distilled under reduced pressure, and the mixture was extracted with methylene chloride; the organic layer was washed with water, dried over sodium sulfate and evaporated to dryness under reduced pressure. The crude product was purified by flash-chromatography (SiO$_2$) using n-hexane/ethyl acetate 80/20 as eluant to give 3.5 g of 3β-(2-tert-butyldimethylsilyloxyethoxy)-17β-( 2-hydroxyethoxy)-17α-(3-furyl)-5β-androstane as a pale yellow solid.

$^1$H NMR (300 MHz, CDCl$_3$, ppm from TMS): 0.06 (6H, s); 0.81–0.90 (12H, m); 1.02 (3H, s); 3.48–3.79 (9H, m); 6.30 (1H, bs); 7.20 (1H, bs); 7.35 (1H, bs).

A solution of 1.2 ml of diethyl azodicarboxylate was added dropwise, under nitrogen, to a solution of 3.0 g of 3β-( 2-tert-butyldimethylsilyloxyethoxy)-17β-(2-hydroxyethoxy)-17α-(3-furyl)-5β-androstane, 1.05 g of phthalimide and 2.0 g of triphenylphosphine in 20 ml of tetrahydrofuran at room temperature. After 2 hrs the solvent was removed in vacuo, the crude product was dried over anhydrous sodium sulfate and evaporated to dryness under reduced pressure. The crude product was purified by flash-chromatography (SiO$_2$) using n-hexane/ethyl acetate 80/20 to give 2.8 g of 3β-( 2-tert-butyldimethylsilyloxyethoxy)-17β-(2-phthalimidoethoxy)-17α-(3-furyl)-5β-androstane.

$^1$H NMR (300 MHz, CDCl$_3$, ppm from TMS): 0.06 (6H, s); 0.80–0.90 (12H, m); 1.02 (3H, s); 3.36–3.75 (9H, m); 6.32 (1H, bs); 7.20 (1H, bs); 7.35 (1H, bs); 7.69–7.92 (4H, m).

Tetrabutylammonium fluoride (20 ml of a solution 1.0M in tetrahydrofuran) was added to a solution of 2.0 g of 3β-( 2-tert-butyldimethylsilyloxyethoxy)-17β-(2-phthalimidoethoxy)-17α-( 3-furyl)-5β-androstane in 20 ml of tetrahydrofuran, the mixture was kept on standing at room temperature for 20 hrs, then poured into water and extracted with methylene chloride. The organic layer was dried over sodium sulfate and evaporated to dryness under reduced pressure and the crude product was purified by flash-chromatography (SiO$_2$) using n-hexane/ethyl acetate 7/3 as eluant to give 1.2 g of 3β-(2-hydroxyethoxy)-17β-( 2-phthalimidoethoxy)-17α-(3-furyl)-5β-androstane as a white solid.

$^1$H-NMR (300 MHz, CDCl$_3$, ppm from TMS): 0.81 (3H, s); 1.02 (3H, s); 3.38–3.76 (9H, m); 6.32 (1H, bs); 7.18 (1H, bs); 7.35 (1H, bs); 7.69–7.92 (4H, m).

To a suspension of 0.80 g of NaH (60% dispersion in mineral oil) in 85 ml of dry tetrahydrofuran 1.0 g of 3β-( 2-hydroxyethoxy)-17β-(2-phthalimidoethoxy)-17α-(3-furyl)-5β-androstane were added at room temperature under nitrogen atmosphere. The mixture was kept at 40° C. for 2 hrs, then 3.2 g of 1-(2-chloroethyl)pyrrolidine were added and the suspension was kept at the same temperature for 4 hrs; 50 ml of water were added cautiously and the tetrahydrofuran was distilled at reduced pressure. The residue was extracted with methylene chloride, the organic layer was dried over anhydrous sodium sulfate and evaporated to dryness under reduced pressure. The crude product was purified by flash-chromatography (SiO$_2$) using methylene chloride/methanol 70/30 as eluant to give 0.80 g of 3β-(2-( 1-pyrrolidinyl)ethoxy)-17β-(2-phthalimidoethoxy)-17α-( 3-furyl)-5β-androstane, as a white solid.

$^1$H-NMR (300 MHz, CDCl$_3$, ppm from TMS): 0.81 (3H, s); 1.01 (3H, s); 2.46–2.86 (6H, m); 3.38–3.75 (11H, m); 6.32 (1H, bs); 7.20 (1H,bs); 7.35 (1H, bs); 7.68–7.92 (4H, m).

To a solution of 0.6 g of 3β-(2-(1-pyrrolidinyl)ethoxy)-17β-( 2-phthalimidoethoxy)-17α-(3-furyl)-5β-androstane in 15 ml of ethanol (96%) 0.3 g of hydrazine hydrate were added at room temperature.

The mixture was kept at reflux for 4 hrs, then 15 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.35 g of the title compound (I-af) as a white solid.

$^1$H-NMR (300 MHz, CDCl$_3$, ppm from TMS): 0.79 (3H, s); 1.01 (3H, s); 2.46–3.02 (8H, m); 3.37–3.78 (9H, m); 6.38 (1H, bs); 7.24 (1H,bs); 7.36 (1H, bs);

EXAMPLE 7

3β-(2-(2-(1-Pyrrolidinyl)ethoxy)ethoxy)-17β-(2-( 1-pyrrolidinyl)ethoxy)-17α-(3-furyl)-5β-androstane (I-ag)

The title compound (I-ag) (0.12 g) was obtained as a white solid from 3β-(2-hydroxyethoxy)-17α-(3-furyl)-5β-androstan-17β-ol (0.10 g) using the same procedure described in Ex. 3, but keeping the reaction at reflux temperature for 24 hrs and using 1-( 2-chloroethyl)pyrrolidine as reactant.

$^1$H-NMR (300 MHz, CDCl$_3$, ppm from TMS): 0.77 (3H, s); 1.02 (3H, s); 2.46–2.81 (12H, m); 3.38 (2H, t); 3.56–3.79 (7H, m); 6.32 (1H,bs); 7.21 (1H, bs); 7.36 (1h, bs).

EXAMPLE 8

3β-(2-Aminoethoxy)-17α-(3-furyl)-androstan-17β-ol (I-ah)

The title compound (I-ah) (0.20 g) was obtained as a pale yellow solid from 3β-(2-hydroxyethoxy)-17α-(3-furyl)-androstan-17β-ol (0.50 g) (prepared as described in Prep 1 starting from 3β-(2-hydroxyethoxy)-androstan-17-one which in turn is obtained as described in Prep. 3) using the same procedure described in Ex. 1 and using phthalimide/triphenylphosphine as reactants.

$^1$H-NMR (300 MHz, CDCl$_3$, ppm from TMS): 0.81 (3H, s); 0.98 (3H, s); 2.80–3.15 (3H, m); 3.35–3.46 (2H, t); 6.40 (7H, bs); 7.25 (1H, bs); 7.48 (1H, bs).

EXAMPLE 9

3β-(3-Aminopropoxy)-17α-(3-furyl)-androstan-17β-ol (I-ai)

The title compound (I-ai) (0.12 g) was obtained as a pale yellow solid from 17α-(3-furyl)-androstane-3β, 17β-diol (0.90 g) (U.S. Pat. No. 3,436,390) using the same procedure described in Ex. 2 and using allyl bromide/9-borabicyclo [3.3.1]nonane/phthalimide /triphenylphosphine as reactants.

$^1$H-NMR (300 MHz, CDCl$_3$, ppm from TMS): 0.81 (3H, s); 0.98 (3H, s); 2.78–3.18 (3H, m); 3.41–3.50 (2H, t); 3.53 (1H, bs); 6.40 (1H, bs); 7.25 (1H, bs); 7.48 (1H, bs).

EXAMPLE 10

3β-(2-(1-Pyrrolidinyl)ethoxyy)-17α-(3-furyl)-androstan-17β-ol (I-aj)

The title compound (I-aj) (0.35 g) was obtained as a white solid from 17α-(3-furyl)-androstane-3β, 17β-diol (0.43 g) (U.S. Pat. No. 3,436,390) using the same procedure described in Ex. 3 and using 1-(2-chloroethyl)pyrrolidine as reactant.

$^1$H-NMR (300 MHz, CDCl$_3$, ppm from TMS): 0.80 (3H, s); 0.98 (3H, s); 2.48–2.70 (6H, m); 3.15–3.26 (1H, m); 3.52–3.63 (2H, t); 6.29 (1H, bs); 7.18 (1H, bs); 7.37 (1H, bs).

EXAMPLE 11

3β, 17β-Bis(2-(1-pyrrolidinyl)ethoxy)-17α-(3-furyl)-androstane (I-ak)

The title compound (I-ak) (0.40 g) was obtained as a pale yellow pasty solid from 17α-(3-furyl)-androstane-3β, 17β-diol (0.60 g) (U.S. Pat. No. 3,436,390) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.75 (3H, s); 0.94 (3H, s); 2.45–2.71 (12H, m); 3.10–3.23 (1H, m); 3.28–3.38 (2H, m); 3.53–3.62 (2H, m); 6.30 (1H, bs); 7.18 (1H, bs); 7.35 (1H, bs).

EXAMPLE 12

3β-(2-(2(1-Pyrrolidinyl)ethoxyy)ethoxy)-17α-(3-furyl)-androstan-17β-ol (I-al)

The title compound (I-al) (0.40 g) was obtained as a pale brown solid from 3β-(2-hydroxyethoxy)-17α-(3-furyl)-androstan- 17β-ol (0.50 g) using the same procedure described in Ex. 3 and using 1-(2-chloroethyl)pyrrolidine as reactant.

$^1$H-NMR (300 MHz, CDCl$_3$, ppm from TMS): 0.81 (3H, s); 0.98 (3H, s); 2.54–2.65 (4H, m); 2.68–2.72 (2H, m); 3.18–3.28 (1H, m); 3.57–3.62 (6H, m); 6.38 (1H, bs); 7.27 (1H, bs); 7.38 (1H, bs).

EXAMPLE 13

3β-(2-(2-(1-Pyrrolidinyl)ethoxy)ethoxy)-17β-( 2-aminoethoxy)-17α-(3-furyl)-androstane (I-am)

The title compound (I-am) (0.20 g) was obtained as a white solid from 3β-(2-tert-butyldimethylsilyloxyethoxy)-17α-( 3-furyl)-androstan-17β-ol (2.5 g) (prepared as described in Prep. 1 starting from 3β-(2-hydroxyethoxy)-androstan-17-one) using the same procedure described in Ex. 6 and using bromoacetaldehyde diethylacetal/phthalimide/triphenylphosphine/1-(2-chloroethyl) pyrrolidine as reactants.

$^1$H-NMR (300 MHz, CDCl$_3$, ppm from TMS): 0.81 (3H, s); 0.98 (3H, s); 2.50–2.75 (8H, m); 3.18–3.29 (1H, m); 3.55–3.62 (8H, m); 6.48 (1H, bs); 7.20 (1H, bs); 7.36 (1H, bs).

EXAMPLE 14

3β-(2-(2-(1-Pyrrolidinyl)ethoxy)ethoxy)-17β-(2-( 1-pyrrolidinyl)ethoxy)-17α-(3-furyl)-androstane (I-an)

The title compound (I-an) (0.22 g) was obtained as a white foam from 3β-(2-hydroxyethoxy)-17α-(3-furyl)-androstan-17β-ol (0.30 g) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.78 (3H, s); 0.91 (3H, s); 2.40–2.80 (12H, m); 3.12–3.29 (1H, m); 3.35 (2H, t); 3.58–379 (6H, m); 6.30 (1H, bs); 7.18 (1H, bs); 7.35 (1H, bs).

EXAMPLE 15

3β-(2-(1-Pyrrolidinyl)ethoxy)-17α-(3-furyl)-androst-4-en-17β-ol (I-ao)

The title compound (I-ao) (0.25 g) was obtained as a white solid from 17α-(3-furyl)-androst-4-ene-3β,17β-diol (0.38 g) (prepared as described in Prep. 2 starting from 3β-hydroxyandrost-4-en-17-one (D'Incan E. et al., *Tetrahedron*, 1982, 38, 1755)) using the same procedure described in Ex. 3 and using 1-(2-chloroethyl)pyrrolidine as reactant.

$^1$H-NMR (300 MHz, CDCl$_3$, ppm from TMS): 0.82 (3H, s); 1.10 (3H, s); 2.48–2.86 (6H, m); 3.75–3.91 (3H, m); 5.30 (1H, bs); 6.38 (1H, bs); 7.25 (1H, bs); 7.38 (1H, bs).

EXAMPLE 16

3β-(2-(2-(1-Pyrrolidinyl)ethoxy)ethoxy)-17α-( 3-furyl)-androst-4-en-17β-ol (I-ap)

The title compound (I-ap) (0.30 g) was obtained as a pale yellow solid from 3β-(2-hydroxyethoxy)-17α-(3-furyl)-androst-4-en-17β-ol (0.48 g) (prepared as described in Prep. 1 starting from 3β-(2-hydroxyethoxy)-androst-4-en-17-one which in turn is obtained as described in Prep. 3 starting from 3β-hydroxyandrost-4-en-17-one) using the same procedure described in Ex. 3 and using 1-(2-chloroethyl)pyrrolidine as reactant.

$^1$H-NMR (300 MHz, CDCl$_3$, ppm from TMS): 0.81 (3H, s); 1.11 (3H, s); 2.47–2.80 (6H, m); 3.38–3.91 (7H, m); 5.31 (1H, bs); 6.38 (1H, bs); 7.24 (1H, bs); 7.37 (1H, bs).

EXAMPLE 17

3β-(2-(2-(1-Pyrrolidinyl)ethoxy)ethoxy)-17α-( 2-aminoethoxy)-17α-(3-furyl)-androst-4-ene (I-aq)

The title compound (I-aq) (0.22 g) was obtained as a white pasty solid from 3β-(2-tert-butyldimethylsilyloxyethoxy)-17α-( 3-furyl)-androst-4-en-17β-ol (3.8 g) (prepared as described in Prep. 1 starting from 3β-(2-hydroxyethoxy)-androst-4-en-17-one) using the same procedure described in Ex. 6 and using bromoacetaldehyde diethylacetal/phthalimide/triphenylphosphine/1-(2-chloroethyl)pyrrolidine as reactants.

$^1$H-NMR (300 MHz, CDCl$_3$, ppm from TMS): 0.80 (3H, s); 1.13 (3H, s); 2.45–2.81 (8H, m); 3.38–3.92 (9H, m); 5.30 (1H, bs); 6.28 (1H, bs); 7.17 (1H, bs); 7.37 (1H, bs).

EXAMPLE 18

3β-(2-(2-(1-Pyrrolidinyl)ethoxy)ethoxy)-17β-(2-( 1-pyrrolidinyl)ethoxy)-17α-(3-furyl)-androst-4-ene (I-ar)

The title compound (I-ar) (0.18 g) was obtained as a white foam from 3β-(2-hydroxyethoxy)-17α-(3-furyl)-androst-4-en- 17β-ol (0.27 g) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.81 (3H, s); 1.12 (3H, s); 2.46–2.86 (12H, m); 3.38–3.93 (9H, m); 5.33 (1H, bs); 6.28 (1H, bs); 7.15 (1H, bs); 7.35 (1H, bs).

EXAMPLE 19

3β-(2-Aminoethoxy)-17α-(3-furyl)-androst-5-en-17β-ol (I-as)

The title compound (I-as) (0.21 g) was obtained as a pale yellow solid from 3β-(2-hydroxyethoxy)-17α-(3-furyl)-androst- 5-en-17β-ol (0.48 g) (Prep. 1) using the same procedure described in Ex. 1 and using phthalimide/triphenylphosphine as reactants.

$^1$H-NMR (300 MHz, CDCl$_3$, ppm from TMS): 0.51 (3H, s); 0.96 (3H, s); 2.80–3.22 (3H, m); 3.36–3.45 (2H, t); 5.39 (1H, m); 6.41 (1H, bs); 7.25 (1H, bs); 7.47 (1H, bs).

EXAMPLE 20

3β-(3-Aminopropoxy)-17α-(3furyl)-androst-5-en- 17β-ol (I-at)

The title compound (I-at) (0.15 g) was obtained as a pale yellow solid from 17α-(3-furyl)-androst-5-ene-3β, 17β-diol (0.88 g) (II-a, Prep. 4) using the same procedure described in Ex. 2 and using allyl bromide/9-borabicyclo[3.3.1]nonane/phthalimide/ triphenylphosphine as reactants.

$^1$H-NMR (300 MHz, CDCl$_3$, ppm from TMS): 0.51 (3H, s); 0.96 (3H, s); 2.79–3.22 (6H, m); 3.37–3.46 (2H, t); 5.38 (1H, m); 6.41 (1H, bs); 7.25 (1H, bs); 7.47 (1H, bs).

EXAMPLE 21

3β-(2-(1-Pyrrolidinyl)ethoxy)-17α-(3-furyl)-androst-5-en-17β-ol (I-au)

The title compound (I-au) (0.27 g) was obtained as a white solid from 17α-(3-furyl)-androst-5-ene-3β,17β-diol (0.48 g) (II-a, Prep. 4) using the same procedure described in Ex. 3 and using 1-(2-chloroethyl)pyrrolidine as reactant.

$^1$H-NMR (300 MHz, CDCl$_3$, ppm from TMS): 0.99 (6H, s); 2.46–3.26 (7H, m); 3.76–3.85 (2H, t); 5.30–5.38 (1H, m); 6.38 (1H, bs); 7.27 (1H, bs); 7.36 (1H, bs).

EXAMPLE 22

3β, 17β-Bis(2-(1-pyrrolidinyl)ethoxy)-17α-(3-furyl)-androst-5-ene (I-av)

The title compound (I-av) (0.30 g) was obtained as a pale yellow solid from 17α-(3-furyl)-androst-5-ene-3β, 17β-diol (0.50 g) (II-a, Prep. 4)using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.51 (3H, s); 0.98 (3H, s); 2.46–2.64 (12H, m); 3.15–3.45 (3H, m); 3.43–3.65 (2H, m); 5.38 (1H, m); 6.30 (1H, bs); 7.20 (1H, bs); 7.36 (1H, bs).

EXAMPLE 23

3β-(2-(2-(1-Pyrrolidinyl)ethoxy)ethoxy)-17α-( 3-furyl)-androst-5-en-17β-ol (I-aw)

The title compound (I-aw) (0.32 g) was obtained as a white solid from 3β-(2-hydroxyethoxy)-17α-(3-furyl)-androst-5-en- 17β-ol (0.48 g) (Prep. 1) using the same procedure described in Ex. 3 and using 1-(2-chloroethyl)pyrrolidine as reactant.

$^1$H-NMR (300 MHz, CDCl$_3$, ppm from TMS): 1.01 (6H, bs); 2.54–2.62 (4H, m); 2.68–2.72 (2H, m); 3.18–3.28 (1H, m); 3.57–3.62 (6H, m); 5.30–5.37 (1H, m); 6.38 (1H, bs); 7.27 (1H, bs); 7.38 (1H, bs).

EXAMPLE 24

3β-(2-(2-(1-Pyrrolidinyl)ethoxy)ethoxy)-17β-( 2-aminoethoxy)-17α-(3-furyl)-androst-5-ene (I-ax)

The title compound (I-ax) (0.18 g) was obtained as a pale brown solid from 3β-(2-tert-butyldimethylsilyloxyethoxy)-17α-( 3-furyl)-androst-5-en-17β-ol (2.2 g) (prepared as described in Prep. 1) using the same procedure described in Ex. 6 and using bromoacetaldehyde diethylacetal/phthalimide/triphenylphosphine/ 1-(2-chloroethyl)pyrrolidine as reactants.

$^1$H-NMR (300 MHz, CDCl$_3$, ppm from TMS): 1.01 (6H, bs); 2.48–3.22 (9H, m); 3.31–3.94 (8H, m); 5.30–5.36 (1H, m); 6.28 (1H, bs); 7.17 (1H, bs); 7.36 (1H, bs).

EXAMPLE 25

3β-(2-(2-(1-pyrrolidinyl)ethoxy)ethoxy)-17β-(2-( 1-pyrrolidinyl)ethoxy)-17α-(3furyl)-androst-5-ene (I-ay)

The title compound (I-ay) (0.22 g) was obtained as a thick oil from 3β-(2-hydroxyethoxy)-17α-(3-furyl)-androst-5-en-17β-ol (0.37 g) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 1.01 (6H, bs); 2.40–2.75 (12H, m); 3.15–3.26 (1H, m); 3.32 (2H, t); 3.48–3.66 (6H, m); 5.30–5.37 (1H, m); 6.29 (1H, bs); 7.18 (1H, bs); 7.36 (1H, bs).

EXAMPLE 26

3β-(2-(2-(1-Pyrrolidinyl)ethoxy)ethoxy)-17α-( 3-thienyl)-5β-androstan-17β-ol (I-az)

The title compound (I-az) (0.35 g) was obtained as a white solid from 3β-(2-hydroxyethoxy)-17α-(3-thienyl)-5β-androstan- 17β-ol (0.41 g) (prepared as described in Prep. 1 starting from 3β-(2-hydroxyethoxy)-5β-androstan-17-one (which in turn is obtained as described in Prep. 3 starting from 3β-hydroxy-5β-androstan-17-one (Elisberg E. et al., *J. Amer. Chem. Soc.*,1952, 74, 2814)) and using 3-bromothiophene as reactant) using the same procedure described in Ex. 3 and using 1-(2-chloroethyl)pyrrolidine as reactant.

$^1$H-NMR (300 MHz, CDCl$_3$, ppm from TMS): 0.82 (3H, s); 1.10 (3H, s); 2.50–2.89 (6H, m); 3.38–3.76 (7H, m); 7.03 (1H, m); 7.09 (1H, m); 7.27 (1H, m).

EXAMPLE 27

3β-(2-(2-(1-Pyrrolidinyl)ethoxy)ethoxy)-17β-(2-( 1-pyrrolidinyl)ethoxy)-17α-(3-thienyl)-5β-androstane (I-ba)

The title compound (I-ba) (0.25 g) was obtained as a white pasty solid from 3β-(2-hydroxyethoxy)-17α-(3-thienyl)- 5β-androstan-17β-ol (0.35 g) (see Ex. 26) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.81 (3H, s); 1.08 (3H, s); 2.46–2.81 (12H, m); 3.37 (2H, t); 3.56–3.79 (7H, m); 6.92 (1H, m); 7.00 (1H, m); 7.25 (1H, m).

EXAMPLE 28

3β-(2-(2-(1-Pyrrolidinyl)ethoxy)ethoxy)-17α-( 3-thienyl)-androstan-17β-ol (I-bb)

The title compound (I-bb) (0.22 g) was obtained as a pale yellow solid from 3β-(2-hydroxyethoxy)-17α-( 3-thienyl)-androstan-17β-ol (0.29 g) (prepared as described in Prep. 1 starting from 3β-(2-hydroxyethoxy)-androstan-17-one and using 3-bromothiophene as reactant) using the same procedure described in Ex. 3 and using 1-(2-chloroethyl)pyrrolidine as reactant.

$^1$H-NMR (300 MHz, CDCl$_3$, ppm from TMS): 0.82 (3H, s); 1.10 (3H, s); 2.47–2.87 (6H, m); 3.12–3.29 (1H, m); 3.38–3.76 (6H, m); 7.03 (1H, m); 7.00 (1H, m); 7.25 (1H, m).

EXAMPLE 29

3β-(2-(2-(1-Pyrrolidinyl)ethoxy)ethoxy)-17β-(2-( 1-pyrrolidinyl)ethoxy)-17α-(3-thienyl)-androstane (I-bc)

The title compound (I-bc) (0.24 g) was obtained as a pale yellow solid from 3β-(2-hydroxyethoxy)-17α-(3-thienyl)-androstan-17β-ol (0.36 g)(see Ex. 28) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.82 (3H, s); 1.12 (3H, s); 2.46–3.28 (13H, m); 3.37–3.75 (8H, m); 6.92 (1H, m); 7.00 (1H, m); 7.26 (1H, m).

EXAMPLE 30

3β-(2-(2-(1-Pyrrolidinyl)ethoxy)ethoxy)-17α-( 3-thienyl)-androst-4-en-17β-ol (I-bd)

The title compound (I-bd) (0.34 g) was obtained as a thick oil from 3β-(2-hydroxyethoxy)-17α-(3-thienyl)-androstan-17β-ol (0.50 g) (prepared as described in Prep. 1 starting from 3β-(2-hydroxyethoxy)-androst-4-en-17-one which in turn is obtained as described in Prep. 3 starting from 3β-hydroxyandrost-4-en-17-one (D'Incan E. et al., *Tetrahedron*, 1982, 38, 1755) and using 3-bromothiophene as reactant) using the same procedure described in Ex. 3 and using 1-(2-chloroethyl)pyrrolidine as reactant.

$^1$H-NMR (300 MHz, CDCl$_3$, ppm from TMS): 0.81 (3H, s); 1.12 (3H, s); 2.48–2.88 (6H, m); 3.38–3.96 (7H, m); 5.30 (1H, m); 7.03 (1H, m); 7.09 (1H, m); 7.27 (1H, m).

EXAMPLE 31

3β-(2-(2-(1-Pyrrolidinyl)ethoxy)ethoxy)-17β-(2-( 1-pyrrolidinyl)ethoxy)-17α-(3-thienyl)-androst-4-ene (I-be)

The title compound (I-be) (0.24 g) was obtained as a white solid from 3β-(2-hydroxyethoxy)-17α-(3-thienyl)-androstan- 17β-ol (0.30 g) (see Ex. 30) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.83 (3H, s); 1.10 (3H, s); 2.46–2.81 (12H, m); 3.35–3.94 (9H, m); 5.30 (1H, bs); 6.93 (1H, m); 7.00 (1H, m); 7.25 (1H, m).

EXAMPLE 32

3β-(2-(2-(1-Pyrrolidinyl)ethoxy)ethoxy)-17α-( 3-thienyl)-androst-5-en-17β-ol (I-bf)

The title compound (I-bf) (0.20 g) was obtained as a white solid from 3β-(2-hydroxyethoxy)-17α-(3-thienyl)-androst-5-en-17β-ol (0.30 g) (prepared as described in Prep. 1 using 3-bromothiophene as reactant) using the same procedure described in Ex. 3 and using 1-(2-chloroethyl)pyrrolidine as reactant.

$^1$H-NMR (300 MHz, CDCl$_3$, ppm from TMS): 1.00 (3H, s); 1.10 (3H, s); 2.44–3.23 (7H, m); 3.32–3.93 (6H, m); 5.31–5.37 (1H, m); 7.03 (1H, m); 7.09 (1H, m); 7.26 (1H, m).

EXAMPLE 33

3β-(2-(2-(1-Pyrrolidinyl)ethoxy)ethoxy)-17β-(2-( 1-pyrrolidinyl)ethoxy)-17α-(3-thienyl)-androst-5-ene (I-bg)

The title compound (I-bg) (0.18 g) was obtained as a white solid from 3β-(2-hydroxyethoxy)-17α-(3-thienyl)-androst- 5-en-17β-ol (0.32 g) (see Ex. 32) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 1.01 (3H, s); 1.09 (3H, s); 2.44–3.25 (13H, m); 3.32–3.94 (8H, m); 5.31–5.37 (1H, m); 6.93 (1H, m); 7.00 (1H, m); 7.25 (1H, m).

EXAMPLE 34

3β-(2-(2-(1-Pyrrolidinyl)ethoxy)ethoxy)-17α-(4-chlorophenyl)-5β-androstan-17β-ol (I-bh)

The title compound (I-bh) (0.16 g) was obtained as a white solid from 3β-(2-hydroxyethoxy)-17α-(4-chlorophenyl)-5β-androstan-17β-ol (0.22 g) (prepared as described in Prep. 1 starting from 3β-(2-hydroxyethoxy)-5β-androstan-17-one which in turn is obtained as described in Prep. 3 starting from 3β-hydroxy-5β-androstan-17-one (Elisberg E. et al., *J.Amer. Chem. Soc.*, 1952, 74, 2814) and using 1-bromo-4-chlorobenzene as reactant) using the same procedure described in Ex. 3 and using 1-(2-chloroethyl)pyrrolidine as reactant.

$^1$H-NMR (300 MHz, CDCl$_3$, ppm from TMS): 0.95 (3H, s); 1.02 (3H, s); 2.46–2.83 (6H, m); 3.37–3.76 (7H, m); 7.10 (2H, d); 7.60 (2H, d).

EXAMPLE 35

3β-(2-(2-(1-Pyrrolidinyl)ethoxy)ethoxy)-17β-(2-(1-pyrrolidinyl)ethoxy)-17α-(4-chlorophenyl)-5β-androstane (I-bi)

The title compound (I-bi) (0.26 g) was obtained as a white solid from 3β-(2-hydroxyethoxy)-17α-(4-chlorophenyl)-5β-androstan-17β-ol (0.42 g) (see Ex. 34) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.95 (3H, s); 1.03 (3H, s); 2.46–2.81 (12H, m); 3.37 (2H, t); 3.56–3.79 (7H, m); 7.10 (2H, d); 7.60 (2H, d).

EXAMPLE 36

3β-(2-(2-(1-Pyrrolidinyl)ethoxy)ethoxy)-17α-(4-chlorophenyl)-androstan-17β-ol (I-bj)

The title compound (I-bj) (0.23 g) was obtained as a white solid from 3β-(2-hydroxyethoxy)-17α-(4-chlorophenyl)-androstan-17β-ol (0.42 g) (prepared as described in Prep. 1 starting from 3β-(2-hydroxyethoxy)-androstan-17-one which in turn is obtained as described in Prep. 3 and using 1-bromo-4-chlorobenzene as reactant) using the same procedure described in Ex. 3 and using 1-(2-chloroethyl)pyrrolidine as reactant.

$^1$H-NMR (300 MHz, CDCl$_3$, ppm from TMS): 0.96 (3H, s); 1.10 (3H, s); 2.45–2.82 (6H, m); 3.12–3.29 (1H, m); 3.39–3.77 (6H, m); 7.11 (2H, d); 7.58 (2H, d).

EXAMPLE 37

3β-(2-(2-(1-Pyrrolidinyl)ethoxy)ethoxy)-17β-(2-(1-pyrrolidinyl)ethoxy)-17α-(4-chlorophenyl)-androstane (I-bk)

The title compound (I-bk) (0.28 g) was obtained as a white solid from 3β-(2-hydroxyethoxy)-17α-(4-chlorophenyl)-androstan-17β-ol (0.45 g) (see Ex. 36) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.98 (3H, s); 1.08 (3H, s); 2.46–3.28 (13H, m); 3.37–3.75 (8H, m); 7.13 (2H, d); 7.61 (2H, d).

EXAMPLE 38

3β-(2-(2-(1-Pyrrolidinyl)ethoxy)ethoxy)-17α-(4-chlorophenyl)-androst-4-en-17β-ol (I-bl)

The title compound (I-bl) (0.25 g) was obtained as a white solid from 3β-(2-hydroxyethoxy)-17α-(4-chlorophenyl)-androst-4-en-17β-ol (0.49 g) (prepared as described in Prep. 1 starting from 3β-(2-hydroxyethoxy)-androst-4-en-17-one which in turn is obtained as described in Prep. 3 starting from 3β-hydroxyandrost-4-en-17-one (D'Incan E. et al., *Tetrahedron*, 1982, 38, 1755) and using 1-bromo-4-chlorobenzene as reactant) using the same procedure described in Ex. 3 and using 1-(2-chloroethyl)pyrrolidine as reactant.

$^1$H-NMR (300 MHz, CDCl$_3$, ppm from TMS): 0.95 (3H, s); 1.11 (3H, s); 2.47–2.86 (6H, m); 3.38–3.96 (7H, m); 5.30 (1H, bs); 7.10 (2H, d); 7.62 (2H, d).

EXAMPLE 39

3β-(2-(2-(1-Pyrrolidinyl)ethoxy)ethoxy)-17β-(2-(1-pyrrolidinyl)ethoxy)-17α-(4-chlorophenyl)-androst-4-ene (I-bm)

The title compound (I-bm) (0.20 g) was obtained as a white solid from 3β-(2-hydroxyethoxy)-17α-(4-chlorophenyl)-androst-4-en-17β-ol (0.35 g) (see Ex. 38) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.95 (3H, s); 1.10 (3H, s); 2.47–2.82 (12H, m); 3.38–3.96 (9H, m); 5.31 (1H, bs); 7.11 (2H, d); 7.62 (2H, d).

EXAMPLE 40

3β-(2-(2-(1-Pyrrolidinyl)ethoxy)ethoxy)-17α-(4-chlorophenyl)-androst-5-en-17β-ol (I-bn)

The title compound (I-bn) (0.28) was obtained as a white solid from 3β-(2-hydroxyethoxy)-17α-(4-chlorophenyl)-androst-5-en-17β-ol (0.43 g) (prepared as described in Prep. 1 using 1-bromo-4-chlorobenzene as reactant) using the same procedure described in Ex. 3 and using 1-(2-chloroethyl)pyrrolidine as reactant.

$^1$H-NMR (300 MHz, CDCl$_3$, ppm from TMS): 0.95 (3H, s); 1.13 (3H, s); 2.44–3.24 (7H, m); 3.32–3.93 (6H, m); 5.31–5.37 (1H, m); 7.09 (2H, d); 7.63 (2H, d).

EXAMPLE 41

3β-(2-(2-(1-Pyrrolidinyl)ethoxy)ethoxy)-17β-(2-(1-pyrrolidinyl)ethoxy)-17α-(4-chlorophenyl)-androst-5-ene (I-bo)

The title compound (I-bo) (0.35 g) was obtained as a white solid from 3β-(2-hydroxyethoxy)-17α-(4-chlorophenyl)-androst-5-en-17β-ol (0.45 g) (see Ex. 40) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.96 (3H, s); 1.12 (3H, s); 2.46–3.22 (13H, m); 3.32–3.94 (8H, m); 5.31–5.37 (1H, m); 7.10 (2H, d); 7.60 (2H, d).

EXAMPLE 42

3β-(2-(2-(1-Pyrrolidinyl)ethoxy)ethoxy)-17α-(4-methoxyphenyl)-5β-androstan-17β-ol (I-bp)

The title compound (I-bp) (0.16 g) was obtained as a white solid from 3β-(2-hydroxyethoxy)-17α-(4-methoxyphenyl)-5β-androstan-17β-ol (0.22 g) (prepared as described in Prep. 1 starting from 3β-(2-hydroxyethoxy)-5β-androstan-17-one which in turn is obtained as described in Prep. 3 starting from 3β-hydroxy-5β-androstan-17-one (Elisberg E. et at., *J. Amer. Chem. Soc.*, 1952,74, 2814) and using 4-bromoanisole as reactant) using the same procedure described in Ex. 3 and using 1-(2-chloroethyl)pyrrolidine as reactant.

$^1$H-NMR (300 MHz, CDCl$_3$, ppm from TMS): 0.95 (3H, s); 1.02 (3H, s); 2.45–2.83 (6H, m); 3.37–3.76 (7H, m); 3.82 (3H, s); 6.70 (2H, d); 7.30 (2H, d).

EXAMPLE 43

3β-(2-(2-(1-Pyrrolidinyl)ethoxy)ethoxy)-17β-(2-(1-pyrrolidinyl)ethoxy)-17α-(4-methoxyphenyl)-5β-androstane (I-bq)

The title compound (I-bq) (0.20 g) was obtained as a white solid from 3β-(2-hydroxyethoxy)-17α-(4-methoxyphenyl)-5β-androstan-17β-ol (0.25 g) (see Ex. 42) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.95 (3H, s); 1.03 (3H, s); 2.46–2.81 (12H, m); 3.37 (2H, t); 3.56–3.78 (7H, m); 3.83 (3H, s); 6.70 (2H, d); 7.30 (2H, d).

EXAMPLE 44

3β-(2-(2-(1-Pyrrolidinyl)ethoxy)ethoxy)-17α-(4-methoxyphenyl)-androstan-17β-ol (I-br)

The title compound (I-br) (0.26 g) was obtained as a white solid from 3β-(2-hydroxyethoxy)-17α-(4-methoxyphenyl)-androstan-17β-ol (0.40 g) (prepared as described in Prep. 1 starting from 3β-(2-hydroxyethoxy)-androstan-17-one which in turn is obtained as described in Prep. 3 and using 4-bromoanisole as reactant) using the same procedure described in Ex. 3 and using 1-(2-chloroethyl)pyrrolidine as reactant.

$^1$H-NMR (300 MHz, CDCl$_3$, ppm from TMS): 0.96 (3H, s); 1.10 (3H, s); 2.47–2.82 (6H, m); 3.14–3.30 (1H, m); 3.39–3.77 (6H, m); 3.82 (3H, s); 6.70 (2H, d); 7.30 (2H, d).

EXAMPLE 45

3β-(2-(2-(1-Pyrrolidinyl)ethoxy)ethoxy)-17β-(2-(1-pyrrolidinyl)ethoxy)-17α-(4-methoxyphenyl)-androstane (I-bs)

The title compound (I-bs) (0.30) was obtained as a white solid from 3β-(2-hydroxyethoxy)-17α-(4-methoxyphenyl)-androstan-17β-ol (0.45 g) (see Ex. 44) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.95 (3H, s); 1.11 (3H, s); 2.46–3.28 (13H, m); 3.36–3.74 (8H, m); 3.80 (3H, s); 6.69 (2H, d); 7.28 (2H, d).

EXAMPLE 46

3β-(2-(2-(1-Pyrrolidinyl)ethoxy)ethoxy)-17α-(4-methoxyphenyl)-androst-4-en-17β-ol (I-bt)

The title compound (I-bt) (0.28 g) was obtained as a white solid from 3β-(2-hydroxyethoxy)-17α-(4-methoxyphenyl)-androst-4-en-17β-ol (0.42 g) (prepared as described in Prep. 1 starting from 3β-(2-hydroxyethoxy)-androst-4-en-17-one which in turn is obtained as described in Prep. 3 starting from 3β-hydroxyandrost-4-en-17-one (D'Incan E. et al., *Tetrahedron*, 1982, 38, 1755) and using 4-bromoanisole as reactant) using the same procedure described in Ex. 3 and using 1-(2-chloroethyl)pyrrolidine as reactant.

$^1$H-NMR (300 MHz, CDCl$_3$, ppm from TMS): 0.94 (3H, s); 1.09 (3H, s); 2.46–2.85 (6H, m); 3.38–3.96 (9H, m); 5.31 (1H, bs); 6.71 (2H, d); 7.32 (2H, d).

EXAMPLE 47

3β-(2-(2-(1-Pyrrolidinyl)ethoxy)ethoxy)-17β-(2-(1-pyrrolidinyl)ethoxy)-17α-(4-methoxyphenyl)-androst-4-ene (I-bu)

The title compound (I-bu) (0.22 g) was obtained as a white solid from 3β-(2-hydroxyethoxy)-17α-(4-methoxyphenyl)-androst-4-en-17β-ol (0.35 g) (see Ex. 46) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.96 (3H, s); 1.07 (3H, s); 2.47–2.83 (12H, m); 3.38–3.96 (12H, m); 5.30 (1H, bs); 6.70 (2H, d); 7.30 (2H, d).

EXAMPLE 48

3β-(2-(2-(1-Pyrrolidinyl)ethoxy)ethoxy)-17α-(4-methoxyphenyl)-androst-5en-17β-ol (I-bv)

The title compound (I-by) (0.26 g) was obtained as a white solid from 3β-(2-hydroxyethoxy)-17α-(4-methoxyphenyl)-androst-5-en-17β-ol (0.40 g) (prepared as described in Prep. 1 using 4-bromoanisole as reactant) using the same procedure described in Ex. 3 and using 1-(2-chloroethyl)pyrrolidine as reactant.

$^1$H-NMR (300 MHz, CDCl$_3$, ppm from TMS): 0.96 (3H, s); 1.10 (3H, s); 2.44–3.24 (7H, m); 3.32–3.94 (10H, m); 5.30–5.35 (1H, m); 6.72 (2H, d); 7.29 (2H, d).

EXAMPLE 49

3β-(2-(2-(1-Pyrrolidinyl)ethoxy)ethoxy)-17β-(2-(1-pyrrolidinyl)ethoxy)-17α-(4-methoxyphenyl)-androst-5-ene (I-bw)

The title compound (I-bw) (0.36 g) was obtained as a white solid from 3β-(2-hydroxyethoxy)-17α-(4-methoxyphenyl)-androst-5-en-17β-ol (0.40 g) (see Ex. 48) using the same procedure described in Ex. 3, but keeping the reaction at reflux temperature for 24 hrs and using 1-(2-chloroethyl)pyrrolidine as reactant.

$^1$H-NMR (300 MHz, CDCl$_3$, ppm from TMS): 0.97 (3H, s); 1.10 (3H, s); 2.45–3.26 (7H, m); 3.33–3.95 (11H, m); 5.30–5.35 (1H, m); 6.74 (2H, d); 7.27 (2H, d).

EXAMPLE 50

3β-(2-(2-(1-Pyrrolidinyl)ethoxy)ethylthio)-17α-( (3-furyl)-5β-androstan-17β-ol (I-bx)

The title compound (I-bx) (0.31 g) was obtained as a white solid from 3β-(2-hydroxyethylthio)-17α-(3-furyl)-5β-androstan- 17β-ol (0.39 g) (prepared as described in Prep. 2 starting from 3β-mercapto-5β-androstan-17-one (Swarm D. A. and Turnbull J. H., *Tetrahedron,* 1966, 22, 231)) using the same procedure described in Ex. 3, but keeping the reaction at room temperature for 2 hrs and using 1-(2-chloroethyl)pyrrolidine as reactant.

$^1$H-NMR (300 MHz, CDCl$_3$, ppm from TMS): 0.81 (3H, s); 1.02 (3H, s); 2.48–2.92 (8H, m); 3.23 (1H, bs); 3.38–3.76 (4H, m); 6.39 (1H, bs); 7.25 (1H, bs); 7.37 (1H, bs).

EXAMPLE 51

3β-(2-(2-(1-Pyrrolidinyl)ethoxy)ethylthio)-17β-(2-( 1-pyrrolidinyl)ethoxy)-17α-(3-furyl)-5β-abdrostane (I-by)

The title compound (I-by) (0.38 g) was obtained as a white solid from 3β-(2-hydroxyethylthio)-17α-(3-furyl)-5β-androstan- 17β-ol (0.45 g) (see Ex. 50) using the same procedure described in Ex. 3, but keeping the reaction at room temperature for 2 hrs and then at reflux temperature for 24 hrs and using 1-(2-chloroethyl)pyrrolidine as reactant.

$^1$H-NMR (300 MHz, CDCl$_3$, ppm from TMS): 0.79 (3H, s); 1.02 (3H, s); 2.46–2.81 (14H, m); 3.24 (1H, bs); 3.56–3.80 (6H, m); 6.32 (1H, bs); 7.20 (1H, bs); 7.36 (1H, bs).

EXAMPLE 52

3β-(2-(2-(1-Pyrrolidinyl)ethoxy)ethylthio)-17α-( (3-furyl)-androstan-17β-ol (I-bz)

The title compound (I-bz) (0.25 g) was obtained as a white solid from 3β-(2-hydroxyethylthio)-17α-(3-furyl)-androstan-17β-ol (0.30 g) (prepared as described in Prep. 2 starting from 3β-mercapto-androstan-17-one (Swann D. A. and Turnbull J. H., *Tetrahedron,* 1964, 20, 265)) using the same procedure described in Ex. 50 and using 1-(2-chloroethyl)pyrrolidine as reactant.

$^1$H-NMR (300 MHz, CDCl$_3$, ppm from TMS): 0.78 (3H, s); 0.92 (3H, s); 2.43–3.00 (9H, m); 3.24 (1H, bs); 3.40–3.76 (4H, m); 6.39 (1H, bs); 7.23 (1H, bs); 7.37 (1H, bs).

EXAMPLE 53

3β-(2-(2-(1-Pyrrolidinyl)ethoxy)ethylthio)-17β-(2-( 1-pyrrolidinyl)ethoxy)-17α-(3-furyl)-androstane (I-ca)

The title compound (I-ca) (0.31 g) was obtained as a white solid from 3β-(2-hydroxyethylthio)-17α-(3-furyl)-androstan-17β-ol (0.40 g) (see Ex. 52) using the same procedure described in Ex. 51 and using 1-(2-chloroethyl)pyrrolidine as reactant.

$^1$H-NMR (300 MHz, CDCl$_3$, ppm from TMS): 0.77 (3H, s); 0.93 (3H, s); 2.44–3.01 (15H, m); 3.39–3.79 (6H, m); 6.40 (1H, bs); 7.26 (1H, bs); 7.38 (1H, bs).

EXAMPLE 54

3β-(2-(2-(1-Pyrrolidinyl)ethoxy)ethylthio)-17α-( (3-furyl)-androst-4-en-17β-ol (I-cb)

The title compound (I-cb) (0.35 g) was obtained as a white solid from 3β-(2-hydroxyethylthio)-17α-(3-furyl)-androst-4-en- 17β-ol (0.50 g) (prepared as described in Prep. 2 starting from 3β-mercapto-androst-4-en-17-one (III-a, Prep. 6)) using the same procedure described in Ex. 50 and using 1-(2-chloroethyl)pyrrolidine as reactant.

$^1$H-NMR (300 MHz, CDCl$_3$, ppm from TMS): 0.80 (3H, s); 1.10 (3H, s); 2.40–2.85 (8H, m); 3.39–3.93 (5H, m); 5.32 (1H, bs); 6.38 (1H, bs); 7.25 (1H, bs); 7.38 (1H, bs).

EXAMPLE 55

3β-(2-(2-(1-Pyrrolidinyl)ethoxy)ethylthio)-17β-( (2-(1-pyrrolidinyl)ethoxy)-17α-(3-furyl)-androst-4-ene (I-cc)

The title compound (I-cc) (0.45 g) was obtained as a white solid from 3β-(2-hydroxyethylthio)-17α-(3-furyl)-androst-4-en- 17β-ol (0.55 g) (see Ex. 54) using the same procedure described in Ex. 51 and using 1-(2-chloroethyl)pyrrolidine as reactant.

$^1$H-NMR (300 MHz, CDCl$_3$, ppm from TMS): 0.80 (3H, s); 1.11 (3H, s); 2.40–2.85 (8H, m); 3.39–3.94 (7H, m); 5.31 (1H, bs); 6.38 (1H, bs); 7.24 (1H, bs); 7.37 (1H, bs).

EXAMPLE 56

3β-(2-(2-(1-Pyrrolidinyl)ethoxy)ethylthio)-17α-( (3-furyl)-androst-5-en-17β-ol (I-cd)

The title compound (I-cd) (0.55 g) was obtained as a white solid from 3β-(2-hydroxyethylthio)-17α-(3-furyl)-androst-5-en- 17β-ol (0.65 g) (Prep. 2) using the same procedure described in Ex. 50 and using 1-(2-chloroethyl)pyrrolidine as reactant.

$^1$H-NMR (300 MHz, CDCl$_3$, ppm from TMS): 0.99 (6H, s); 2.46–2.83 (9H, m); 3.31–3.94 (4H, m); 5.31–5.36 (1H, m); 6.38 (1H, bs); 7.17 (1H, bs); 7.36 (1H, bs).

EXAMPLE 57

3β-(2-(2-(1-Pyrrolidinyl)ethoxy)ethylthio)-17β-( (2-(1-pyrrolidinyl)ethoxy)-17α-(3-furyl)-androst-5-ene (I-ce)

The title compound (I-ce) (0.50 g) was obtained as a white solid from 3β-(2-hydroxyethylthio)-17α-(3-furyl)-androst-5-en- 17β-ol (0.60 g) (see Ex. 56) using the same procedure described in Ex. 50 and using 1-(2-chloroethyl)pyrrolidine as reactant.

$^1$H-NMR (300 MHz, CDCl$_3$, ppm from TMS): 1.01 (6H, s); 2.48–2.88 (15H, m); 3.31–3.94 (6H, m); 5.30–5.36 (1H, m); 6.28 (1H, bs); 7.17 (1H, bs); 7.34 (1H, bs).

PREPARATION OF INTERMEDIATES

PREPARATION 1

3β-(2-Hydroxyethoxy)-17α-(3-furyl)-androst-5-en-17β-ol

To a solution of 2.0 g of 3β-(2-hydroxyethoxy)-androst-5-en- 17-one (Julia S. et al., *Bull. Soc. Chim. France,* 1960, 297) in 20 ml of dimethylformamide, 3.5 g of imidazole and 4.0 g of t-butyldimethylsilyl chloride were added at 0° C. After 12 hrs the mixture was poured into water and extracted with ethyl acetate. The organic layer was dried over sodium sulfate and evaporated to dryness under reduced pressure to give 2.5 g of crude 3β-( 2-tert-butyldimethylsilyloxyethoxy)-androst-5-en-17-one.

To a solution of 7.0 g of 3-bromofuran in 15 ml of dry tetrahydrofuran, kept at −78° C. and under nitrogen, 20.0 ml of butyllithium 2.0M solution in tetrahydrofuran were added; after 1 hr a solution of 2.0 g of 3β-(2-tert-butyldimethylsilyloxyethoxy)-androst-5-en-17-one in 10.0 ml of dry tetrahydrofuran were added. The mixture was kept on standing at −78° C. for 2 hrs and then poured into water and extracted with methylene chloride. The organic layer was dried over sodium sulfate and evaporated to dryness under reduced pressure and the crude product was purified by flash-chromatography (SiO$_2$) using n-hexane/ethyl acetate 8/2 as eluant to give 2.20 g of 3β-( 2-tert-butyldimethylsilyloxyethoxy)-17α-(3-furyl)-androst- 5-en-17β-ol as a white solid.

$^1$H-NMR (300 MHz, CDCl$_3$, ppm from TMS): 0.080 (6H, s); 0.79 (3H, s); 0.95 (9H, s); 1.08 (3H, s); 3.22 (1H, m); 3.52 (2H, t); 3.72 (2H, t); 5.36 (1H, m); 6.40 (1H, bs); 7.25 (1H, bs); 7.38 (1H, bs).

Tetrabutylammonium fluoride (12.1 ml of a solution 1.0M in tetrahydrofuran) was added to a solution of 1.4 g of 3β-( 2-tert-butyldimethylsilyloxyethoxy)-17α-(3-furyl)-androst-5-en-17β-ol in 20 ml of tetrahydrofuran, the mixture was kept on standing at room temperature for 20 hrs, then poured into water and extracted with methylene chloride. The organic layer was dried over sodium sulfate and evaporated to dryness under reduced pressure and the crude product was purified by flash-chromatography (SiO$_2$) using n-hexane/ ethyl acetate 7/3 as eluant to give 1.0 g of the title compound as a white solid.

$^1$H-NMR (300 MHz, CDCl$_3$, ppm from TMS): 0.79 (3H, s); 1.08 (3H, s); 3.22 (1H, m); 3.58 (2H, t); 3.72 (2H, t); 5.36 (1H, m); 6.40 (1H, bs); 7.25 (1H, bs); 7.38 (1H, bs).

PREPARATION 2

3β-(2-Hydroxyethylthio)-17α-(3-furyl)-androst-5-en-17β-ol

To a solution of 2.0 g of 3β-mercapto-androst-5-en-17-one (Swann D. A. and Turnbull J. H., *Tetrahedron*, 1966, 22, 231) and 0.33 ml of 2-chloroethanol in 5.0 ml of tetrahydrofuran under nitrogen atmosphere at room temperature, 0.030 g of sodium hydride (60% dispersion in mineral oil) were added. The reaction mixture was stirred for 3 hrs, diluted with water and extracted with ethyl acetate; the organic layer was dried over sodium sulfate and evaporated to dryness under reduced pressure. The crude product was purified by flash-chromatography (SiO$_2$) using methylene chloride/methanol/30% ammonia solution 95/5/1 as eluant to give 1.2 g of 3β-(2-hydroxyethylthio)-androst- 5-en-17-one.

$^1$H-NMR (300 MHz, CDCl$_3$, ppm from TMS): 0.82 (3H, s); 1.09 (3H, s); 2.81 (1H, m); 2.43 (1H, dd); 2.53 (2H, t); 3.58 (2H, t); 5.36 (1H, m).

To a solution of 1.0 g of 3β-(2-hydroxyethylthio)-androst-5-en-17-one in 20 ml of dimethylformamide, 1.7 g of imidazole and 2.0 g of t-butyldimethylsilyl chloride were added at 0° C. After 12 hrs the mixture was poured into water and extracted with ethyl acetate. The organic layer was dried over sodium sulfate and evaporated to dryness under reduced pressure to give 1.2 g of crude 3β-(2-tert-butyldimethylsilyloxyethio)-androst- 5-en-17-one.

To a solution of 3.5 g of 3-bromofuran in 10 ml of dry tetrahydrofuran, kept at −78° C. and under nitrogen, 10.0 ml of butyllithium 2.0M solution in tetrahydrofuran were added; after 1 hr a solution of 1.0 g of 3β-(2-tert-butyldimethylsilyloxyethio)-androst-5-en-17-one in 5.0 ml of dry tetrahydrofuran were added. The mixture was kept on standing at −78° C. for 2 hrs and then poured into water and extracted with methylene chloride. The organic layer was dried over sodium sulfate and evaporated to dryness under reduced pressure and the crude product was purified by flash-chromatography (SiO$_2$) using n-hexane/ethyl acetate 85/15 as eluant to give 0.9 g of 3β-(2- tert-butyldimethyisilyloxyethylthio)- 17α-(3-furyl)-androst-5-en-17β-ol as a white solid.

$^1$H-NMR (300MHz, CDCl$_3$, ppm from TMS): 0.060 (6H, s); 0.79 (3H, s); 0.91 (3H, s); 0.95 (9H, s); 2.53 (2H, t); 3.23 (1H, m); 3.50 (2H, t); 6.47 (1H, bs); 7.25 (1H, bs); 7.38 (1H, bs).

Tetrabutylammonium fluoride (4.3 ml of a solution 1.0M in tetrahydrofuran) was added to a solution of 0.8 g of 3β-( 2-tert-butyldimethylsilyloxyethylthio)-17α-(3-furyl)-androst-5-en-17β-ol in 20 ml of tetrahydrofuran, the mixture was kept on standing at room temperature for 18 hrs, then poured into water and extracted with methylene chloride. The organic layer was dried over sodium sulfate and evaporated to dryness under reduced pressure and the crude product was purified by flash-chromatography (SiO$_2$) using n-hexane/ethyl acetate 75/25 as eluant to give 0.45 of the title compound as a white solid.

$^1$H-NMR (300MHz, CDCl$_3$, ppm from TMS): 0.79 (3H, s); 1.09 (3H, s); 2.53 (2H, t); 2.81 (1H, m); 3.58 (2H, t); 5.36 (1H, m); 6.40 (1H, bs); 7.25 (1H, bs); 7.38 (1H, bs)

PREPARATION 3

3β-(2-Hydroxyethoxy)-androstan-17-one

A solution of 10.0 g of 3β-hydroxyandrostan-17-one (Elisberg E. et al., *J. Amer. Chem. Soc.*, 1952, 74, 2814) and 0.10 g of p-toluensolfonic acid in 50 ml of benzene and 10 ml of ethylene glycol was kept on standing at reflux temperature for 10 hrs (water was removed by azeotropic distillation). The mixture was pured into water and extracted with ethyl acetate. The organic layer was dried over sodium sulfate, evaporated to dryness under reduced pressure and the crude product was purified by flash-chromatography (SiO$_2$) using n-hexane/ethyl acetate 80/20 as eluant to give 9.0 g of 17-ethylenedioxy-androstan-3β-ol as a colourless oil.

$^1$H-NMR (300MHz, CDCl$_3$, ppm from TMS): 0.83 (3H, s); 0.87 (3H, s); 3.6 (1H, m); 3.81–4.01 (4H, m).

To a suspension of 5.5 g of NaH (60% dispersion in mineral oil) in 400 ml of dry tetrahydrofuran 8.5 g of 17-ethylenedioxy-androstan-3β-ol were added at room temperature under nitrogen atmosphere. The mixture was kept at 40° C. for 2 hrs, then 26 ml of bromoacetaldehyde diethylacetal were added and the suspension was kept at the same temperature for 4 hrs; 50 ml of water were added cautiously, and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$) using n-hexane/ethyl acetate 80/20 as eluant to give 7.5 g of 3β-(2,2-diethoxyethoxy)-17-ethylenedioxy-androstane as a thick oil.

$^1$H-NMR (300MHz, CDCl$_3$, ppm from TMS): 0.83 (3H, s); 0.87 (3H, s); 3.28 (3H, m); 3.27 (1H, m); 3.36 (2H, dd); 3.52–4.00 (8H, m); 4.62 (1H, t).

A solution of 7.2 g of 3β-(2,2-diethoxyethoxy)-17-ethylenedioxy-androstane, in 250 ml of dioxane and 250 ml of a saturated solution of tartaric acid was heated at 70° C. for 2 hrs in a nitrogen atmosphere, 100 ml of water were then added and the residue was extracted with methylene chloride. The organic layer was washed with water, dried over anhydrous sodium sulfate and evaporated to dryness under reduced pressure. The crude product was purified by flash-chromatography (SiO$_2$) using as eluant n-hexane/ethyl acetate 70/30 to give 4.5 g of 3β-formylmethoxy-androstan-17-one as a white solid.

¹H NMR: (300MHz, CDCl₃, ppm from TMS): 0.83 (3H, s); 0.87 (3H, s); 2.45 (1H, dd); 3.27 (1H, m); 4.06 (2H, bs); 9.78 (1H, bs).

To a solution of 4.0 g of 3β-formylmethoxy-androstan-17-one in 50 ml of methanol 0.60 g of sodium borohydride were added slowly at −78° C. After ½ hr 20 ml of water were added, the methanol was distilled under reduced pressure, and the mixture was extracted with methylene chloride; the organic layer was washed with water, dried over sodium sulfate and evaporated to dryness under reduced pressure. The crude product was purified by flash-chromatography (SiO₂) using n-hexane/ethyl acetate 80/20 as eluant to give 3.5 g of the title compound as a white solid.

¹H NMR (300MHz, CDCl₃, ppm from TMS): 0.83 (3H, s); 0.87 (3H, s); 2.45 (1H, dd); 3.27 (1H, m); 3.60 (2H, t); 3.72 (2H, t);.

PREPARATION 4

17α-(3-Furyl)-androst-5-ene-3β, 17β-diol (II-a)

To a solution of 1.0 g of 3β-hydroxyandrost-5-en-17-one (Coffey S. in Rodd's Chemistry of Carbon Compounds, 1970, IID, 257) in 10 ml of dimethylformamide, 1.7 g of imidazole and 1.95 g of t-butyldimethylsilyl chloride were added at 0° C. After 12 hrs the mixture was poured into water and extracted with ethyl acetate. The organic layer was dried over sodium sulfate and evaporated to dryness under reduced pressure to give 1.3 g of crude 3β-tert-butyldimethylsilyloxy-androst-5-en-17-one To a solution of 3.65 g of 3-bromofuran in 10 ml of dry tetrahydrofuran, kept at −78° C. and under nitrogen, 11.0 ml of butyllithium 2.0M solution in tetrahydrofuran were added; after 1 hr a solution of 1.0 g of 3β-tert-butyldimethylsilyloxy-androst-5-en-17-one in 5.0 ml of dry tetrahydrofuran was added. The mixture was kept on standing at −78° C. for 2 hrs and then poured into water and extracted with methylene chloride. The organic layer was dried over sodium sulfate and evaporated to dryness under reduced pressure; the crude product was purified by flash-chromatography (SiO₂) using n-hexane/ethyl acetate 9/1 as eluant to give 0.6 g of 3β-tert-butyldimethylsilyloxy-17α-(3-furyl)-androst-5-en-17β-ol as a white solid.

¹H-NMR (300MHz, CDCl₃, ppm from TMS): 0.040 (6H, s); 0.79 (3H, s); 0.95 (9H, s); 1.09 (3H, s); 3.39 (1H, bs); 5.31–5.41 (1H, d); 6.39 (1H, bs); 7.25 (1H, bs); 7.38 (1H, bs).

Tetrabutylammonium fluoride (6.3 ml of a solution 1.0M in tetrahydrofuran) was added to a solution of 0.6 g of 3β-tert-butyldimethylsilyloxy17α-(3-furyl)-androst-5-en-17β-ol in 10 ml of tetrahydrofuran, the mixture was kept on standing at room temperature for 24 hrs, then poured into water and extracted with methylene chloride. The organic layer was dried over sodium sulfate and evaporated to dryness under reduced pressure and the crude product was purified by flash-chromatography (SiO₂) using n-hexane/ethyl acetate 9/1 as eluant to give 0.45 g of the title compound as a white solid.

¹H-NMR (300MHz, CDCl₃, ppm from TMS): 0.81 (3H, s); 1.08 (3H, s); 3.48 (1H, bs); 5.31–5.41 (1H, d); 6.39 (1H, bs); 7.25 (1H, bs); 7.38 (1H, bs).

PREPARATION 5

3β-Mercapto-17α-(3-furyl)-androst-5-en-17β-ol (II-b)

To a solution of 3.1 g of 3-bromofuran in 10 ml of dry tetrahydrofuran, kept at −78° C. and under nitrogen, 10.0 ml of butyllithium 2.0M solution in tetrahydrofuran were added; after 1 hr a solution of 1.0 g of 3β-mercapto-androst-5-en-17-one (Swann D. A. and Turnbull J. H., Tetrahedron, 1964, 20, 265) in 5.0 ml of dry tetrahydrofuran was added. The mixture was kept at −78° C. for 2 hrs and then poured into water and extracted with methylene chloride. The organic layer was dried over sodium sulfate and evaporated to dryness under reduced pressure and the crude product was purified by flash-chromatography (SiO₂)using n-hexane/ethyl acetate 9/1 as eluant to give 0.45 g of the title compound as a white solid.

¹H-NMR (300MHz, CDCl₃, ppm from TMS): 0.79 (3H, s); 1.08 (3H, s); 3.32 (1H, bs); 5.30–5.42 (1H, d); 6.39 (1H, bs); 7.25 (1H, bs); 7.38 (1H, bs).

PREPARATION 6

3β-Mercapto-androst-4-en-17-one (III-a)

A solution of 1.3 g of 3β-acetylthio-androst-4-en-17-one (IV-a, Prep 7) in 20 ml of methanol, was saturated with gaseous ammonia and kept on standing for 3 hrs at room temperature. The mixture was evaporated to dryness under reduced pressure and purified by flash-chromatography (SiO₂) using n-hexane/ethyl acetate 95/5 as eluant to give 1.1 g of the title compound (IIIa) as a white solid.

¹H-NMR (300MHz, CDCl₃, ppm from TMS): 0.83 (3H, s); 1.09 (3H, s); 2.43 (1H, dd); 3.39 (1H, m); 5.32 (1H, bs).

PREPARATION 7

3β-Acetylthio-androst-4-en-17-one (IV-a)

Diisopropyl azodicarboxylate (3.3 ml) was added to a solution of 4.5 g of triphenylphosphine in 90 ml of tetrahydrofuran at 0 ° C. and the mixture was stirred for 30'. To this mixture a solution of 2.1 g of 3α-hydroxy-androst-4-en-17-one (D'Incan E., Tetrahedron, 1982, 38, 1755) and 2.1 ml of thiolacetic acid in 90 ml of tetrahydrofuran was added dropwise and the residue was stirred for 1 hr at room temperature. The solvent was evaporated to dryness under reduced pressure and the crude product was purified by flash-chromatography (SiO₂) using n-hexane/ethyl acetate 95/5 as eluant to give 1.4 g of the title compound (IV-a) as a white solid.

¹H-NMR (300MHz, CDCl₃, ppm from TMS): 0.83 (3H, s); 1.10 (3H, s); 2.32 (3H, s); 2.44 (1H, dd); 3.89 (1H, m); 5.32 (1H, bs).

I claim:

1. A cyclopentanperhydrophenanthren- 17-(hydroxy or alkoxy)-17-(aryl or heterocyclyl)-3β-derivative of formula (I):

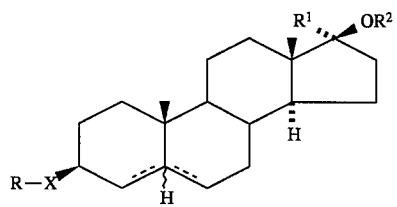

wherein:

the symbol  means that the hydrogen in position 5 can have an α or β configuration;

the symbol  represents either a single or a double bond;

X is O or S;

R is C2–C6 alkyl or C3–C6 alkenyl, substituted by a quaternary ammonium group or one or more $OR^3$, $NR^4R^5$ or C (NH) $NR^6R^7$, wherein $R^3$ is C2–C4 alkyl substituted by an aldehyde group, one or more $NR^6R^7$ or by $NR^6R^7$ and hydroxy;

$R^4$, $R^5$ are independently hydrogen, methyl, C2–C6 alkyl or C3–C6 alkenyl unsubstituted or substituted by one or more $NR^6R^7$, or $NR^6R^7$ and hydroxy, or $R^4$ and $R^5$ taken together with the nitrogen atom form an unsubstituted or substituted saturated or unsaturated five- or six-membered heteromonocyclic ring optionally containing another heteroatom chosen from oxygen or sulfur or nitrogen, or $R^4$ is hydrogen and $R^5$ is $C(NH)NH2$;

$R^6$, $R^7$ are independently hydrogen, C1–C4 alkyl optionally substituted by one or more hydroxy or amino group, or $R^6$ and $R^7$ taken together form, with the nitrogen they are linked to, a saturated or unsaturated five- or six-membered monoheterocyclic ring;

$R^1$ is a monoheterocyclic ring selected from the group consisting of 1,3-dithian-2-yl, furyl, tetrahydrofuryl, thienyl, pyrrolyl, pyridyl, pyridyl-N-oxide, pyrimidyl, pyridazynil, piperidyl, 2-oxo-(1H)-pyridyl, 2-oxo-(2H)-5-pyranyl, 2-oxo-(5H)-4-pyrrolyl, 1-amino-2-oxo-(5H)-3-pyrrolyl, imidazoly, thiazoyl, and oxazolyl;

$R^2$ is hydrogen, methyl, C2–C6 alkyl or C3–C6 alkenyl, unsubstituted or substituted by a quaternary ammonium group or one or more $OR^3$, $NR^4R^5$, $C(NH)NR^6R^7$.

2. A pharmaceutically acceptable salt of a compound of formula (I) of claim 1.

3. A compound according to claim 1, which is selected from:

3β-(2-Aminoethoxy)-17α-(3-furyl)-5β-androstan-17β-ol
3β-(3-Aminopropoxy)-17α-(3-furyl)-5β-androstan-17β-ol
3β,17β-Bis(2-aminoethoxy)-17α-(3-furyl)-5β-androstane
3β-(2-Aminoethoxy)-17β-(2-(1-pyrrolidinyl)ethoxy)-17α-(3-furyl)-5β-androstane
3β-(2-(1-Pyrrolidinyl)ethoxy)-17α-(3-furyl)-5β-androstan-17β-ol
3β-(2-(1-Pyrrolidinyl)ethoxy)-17β-(2-aminoethoxy)-17α-(3-furyl)-5β-androstane
3β,17β-Bis(2-(1-pyrrolidinyl)ethoxy)-17α-(3-furyl)-5β-androstane
3β-(2-(2-(1-Pyrrolidinyl)ethoxy)ethoxy)-17α-(3-furyl)-5β-androstan-17β-ol
3β-(2-(2-(1-Pyrrolidinyl)ethoxy)ethoxy)-17β-(2-aminoethoxy)-17α-(3-furyl)-5β-androstane
3β-(2-(2-(1-Pyrrolidinyl)ethoxy)ethoxy)-17β-(2-(1-pyrrolidinyl)ethoxy)-17α-(3-furyl)-5β-androstane
3β-(2-Aminoethoxy)-17α-(3-furyl)-androstan-17β-ol
3β-(3-Aminopropoxy)-17α-(3-furyl)-androstan-17β-ol
3β,17β-Bis(2-aminoethoxy)-17α-(3-furyl)-androstane
3β-(2-Aminoethoxy)-17β-(2-(1-pyrrolidinylethoxy)-17α-(3-furyl)-androstane
3β-(2-(1-Pyrrolidinyl)ethoxy)-17α-(3-furyl)-androstan-17β-ol
3β-(2-(1-Pyrrolidinyl)ethoxy)-17β-(2-aminoethoxy)-17α-(3-furyl)-androstane
3β,17β-Bis(2-(1-pyrrolidinyl)ethoxy)-17α-(3-furyl)-androstane
3β-(2-(2-(1-Pyrrolidinyl)ethoxy)ethoxy)-17α-(3-furyl)-androstan-17βol
3β-(2-(2-(1-Pyrrolidinyl)ethoxy)ethoxy)-17β-(2-aminoethoxy)-17α-( 3-furyl)-androstane
3β-(2-(2-(1-Pyrrolidinyl)ethoxy)ethoxy)-17β-(2-(1-pyrrolidinyl)ethoxy)- 17α-(3-furyl)-androstane
3β-(2-Aminoethoxy)-17α-(3-furyl)-androst-4-en-17β-ol
3β,17β-Bis(2-aminoethoxy)-17α-(3-furyl)-androst-4-ene
3β-(2-Aminoethoxy)-17β-(2-(1-pyrrolidinylethoxy)-17α-(3-furyl)-androst-4-ene
3β-(2-(1-Pyrrolidinyl)ethoxy)-17α-(3-furyl)-androst-4-en-17β-ol
3β-(2-(1-Pyrrolidinyl)ethoxy)-17β-(2-aminoethoxy)-17α-(3-furyl)-androst-4-ene
3β,17β-Bis(2-(1-pyrrolidinyl)ethoxy)-17α-(3-furyl)-androst-4-ene
3β-(2-(2-(1-Pyrrolidinyl)ethoxy)ethoxy)-17α-(3-furyl)-androst-4-en-17β-ol
3β-(2-(2-(1-Pyrrolidinyl)ethoxy)ethoxy)-17β-(2-aminoethoxy)- 17α-(3-furyl)-androst-4-ene
3β-(2-(2-(1-Pyrrolidinyl)ethoxy)ethoxy)-17β-(2-( 1-pyrrolidinyl)ethoxy)-17α-(3-furyl)-androst-4-ene
3β-(2-Aminoethoxy)-17α-(3-furyl)-androst-5-en-17β-ol
3β-(2-Aminopropoxy)-17α-(3-furyl)-androst-5-en-17β-ol
3β,17β-Bis(2-aminoethoxy)-17α-(3-furyl)-androst-5-ene
3β-(2-Aminoethoxy)-17β-(2-(1-pyrrolidinylethoxy)-17α-(3-furyl)-androst-5-ene
3β-(2-(1-Pyrrolidinyl)ethoxy)-17α-(3-furyl)-androst-5-en-17β-ol
3β-(2-(1-Pyrrolidinyl)ethoxy)-17β-(2-aminoethoxy)-17α-(3-furyl)-androst-5-ene
3β-,17β-Bis(2-(1-pyrrolidinyl)ethoxy)-17α-(3-furyl)-androst-5-ene
3β-(2-(2-(1-Pyrrolidinyl)ethoxy)ethoxy)-17α-(3-furyl)-androst-5-en-17β-ol
3β-(2-(2-(1-Pyrrolidinyl)ethoxy)ethoxy)-17β-( 2-aminoethoxy)-17α-(3-furyl)-androst-5-ene, or
3β-(2-(2-(1-Pyrrolidinyl)ethoxy)ethoxy)-17β-(2-( 1-pyrrolidinyl)ethoxy)-17α-(3-furyl)-androst-5-ene.

4. A compound of formula (I) or a salt thereof, as defined in claim 1 for use in the treatment of the human or animal body by therapy.

5. A pharmaceutical composition containing a pharmaceutically acceptable carrier and/or diluent and as active ingredient a compound of formula (I) of claim 1 or a pharmaceutically acceptable salt thereof.

6. An orally or parenterally administrable pharmaceutical composition for the treatment of cardiovascular disorders comprising an effective amount of a compound of formula (I) of claim 1 or an equivalent amount of a pharmaceutically acceptable salt thereof and an excipient therefor.

7. The composition of claim 6 for the treatment of hypertension.

8. The composition of claim 6 for the treatment of cardiac failure.

9. 3β-17β-bis(2-(1-pyrrolidinyl)ethoxy)-17α-( 3-furyl)-androstane.

* * * * *